United States Patent
Gorochow et al.

(10) Patent No.: US 11,602,350 B2
(45) Date of Patent: Mar. 14, 2023

(54) INTRASACCULAR INVERTING BRAID WITH HIGHLY FLEXIBLE FILL MATERIAL

(71) Applicant: DePuy Synthes Products, Inc., Raynham, MA (US)

(72) Inventors: Lacey Gorochow, Raynham, MA (US); Juan Lorenzo, Raynham, MA (US); Ruijiao Xu, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/703,973

(22) Filed: Dec. 5, 2019

(65) Prior Publication Data

US 2021/0169495 A1 Jun. 10, 2021

(51) Int. Cl.
*A61B 17/12* (2006.01)
*A61B 17/00* (2006.01)

(52) U.S. Cl.
CPC .. *A61B 17/12113* (2013.01); *A61B 17/12031* (2013.01); *A61B 17/12145* (2013.01); *A61B 2017/00867* (2013.01); *A61B 2017/1205* (2013.01)

(58) Field of Classification Search
CPC ........ A61B 17/12113; A61B 17/12031; A61B 17/12145; A61B 17/12171; A61B 17/12168; A61B 17/1204; A61B 17/12109; A61B 17/12177; A61B 17/12022; A61B 17/221; A61B 2017/00867; A61B 2017/1205
USPC ........................................................ 606/200
See application file for complete search history.

(56) References Cited

U.S. PATENT DOCUMENTS

| | | | |
|---|---|---|---|
| 2,849,002 | A | 8/1958 | Oddo |
| 3,480,017 | A | 11/1969 | Shute |
| 4,085,757 | A | 4/1978 | Pevsner |
| 4,282,875 | A | 4/1981 | Serbinenko et al. |
| 4,364,392 | A | 12/1982 | Strother et al. |

(Continued)

FOREIGN PATENT DOCUMENTS

| | | |
|---|---|---|
| CA | 2395796 A1 | 7/2001 |
| CA | 2 431 594 A1 | 9/2002 |

(Continued)

OTHER PUBLICATIONS

Extended European Search Report dated May 2, 2019 in corresponding European Application No. 18214052.5.

(Continued)

*Primary Examiner* — Katherine M Shi
(74) *Attorney, Agent, or Firm* — Troutman Pepper Hamilton Sanders LLP

(57) ABSTRACT

A tubular braided implant is provided including a braid that can be delivered as a single layer braid, invert into itself during deployment to form at least two nested sacks and include additional braid material that can fill the innermost sack. The additional braid material can loop or coil like a ribbon and/or invert to form smaller and smaller nested sacks. The braid can have a variable braid angle along its length such that when positioned for delivery, the can have a high braid angle near its distal end and a low braid angle near the proximal end. In addition, or as a replacement for the braid material that fills the innermost sack, the implant can include an embolic coil that can loop within the innermost sack.

11 Claims, 9 Drawing Sheets

(56) References Cited

U.S. PATENT DOCUMENTS

| | | | |
|---|---|---|---|
| 4,395,806 | A | 8/1983 | Wonder et al. |
| 4,517,979 | A | 5/1985 | Pecenka |
| 4,545,367 | A | 10/1985 | Tucci |
| 4,836,204 | A | 6/1989 | Landymore et al. |
| 4,991,602 | A | 2/1991 | Amplatz et al. |
| 5,002,556 | A | 3/1991 | Ishida et al. |
| 5,025,060 | A | 6/1991 | Yabuta et al. |
| 5,065,772 | A | 11/1991 | Cox, Jr. |
| 5,067,489 | A | 11/1991 | Lind |
| 5,122,136 | A | 6/1992 | Guglielmi et al. |
| 5,192,301 | A | 3/1993 | Kamiya et al. |
| 5,261,916 | A | 11/1993 | Engelson |
| 5,304,195 | A | 4/1994 | Twyford, Jr. et al. |
| 5,334,210 | A | 8/1994 | Gianturco |
| 5,350,397 | A | 9/1994 | Palermo |
| 5,423,829 | A | 6/1995 | Pham et al. |
| 5,624,449 | A | 4/1997 | Pham et al. |
| 5,645,558 | A | 7/1997 | Horton |
| 5,733,294 | A | 3/1998 | Forber et al. |
| 5,891,128 | A | 4/1999 | Gia et al. |
| 5,916,235 | A | 6/1999 | Guglielmi |
| 5,928,260 | A | 7/1999 | Chin et al. |
| 5,935,148 | A | 8/1999 | Villar |
| 5,941,249 | A | 8/1999 | Maynard |
| 5,951,599 | A | 9/1999 | McCrory |
| 5,964,797 | A * | 10/1999 | Ho ............... A61B 17/12022 606/194 |
| 6,007,573 | A | 12/1999 | Wallace et al. |
| 6,024,756 | A | 2/2000 | Pham |
| 6,036,720 | A | 3/2000 | Abrams |
| 6,063,070 | A | 5/2000 | Eder |
| 6,063,100 | A | 5/2000 | Diaz et al. |
| 6,063,104 | A | 5/2000 | Villar |
| 6,080,191 | A | 6/2000 | Thaler |
| 6,086,577 | A | 7/2000 | Ken et al. |
| 6,096,021 | A | 8/2000 | Helm et al. |
| 6,113,609 | A | 9/2000 | Adams |
| 6,123,714 | A | 9/2000 | Gia et al. |
| 6,168,615 | B1 | 1/2001 | Ken |
| 6,168,622 | B1 | 1/2001 | Mazzocchi |
| 6,193,708 | B1 | 2/2001 | Ken et al. |
| 6,221,086 | B1 | 4/2001 | Forber |
| 6,270,515 | B1 | 8/2001 | Linden et al. |
| 6,315,787 | B1 | 11/2001 | Tsugita et al. |
| 6,331,184 | B1 | 12/2001 | Abrams |
| 6,334,048 | B1 | 12/2001 | Edvardsson et al. |
| 6,346,117 | B1 | 2/2002 | Greenhalgh |
| 6,350,270 | B1 | 2/2002 | Roue |
| 6,375,606 | B1 | 4/2002 | Garbaldi et al. |
| 6,375,668 | B1 | 4/2002 | Gifford |
| 6,379,329 | B1 | 4/2002 | Naglreiter et al. |
| 6,391,037 | B1 | 5/2002 | Greenhalgh |
| 6,419,686 | B1 | 7/2002 | McLeod et al. |
| 6,428,558 | B1 | 8/2002 | Jones |
| 6,454,780 | B1 | 9/2002 | Wallace |
| 6,463,317 | B1 | 10/2002 | Kucharczyk et al. |
| 6,506,204 | B2 | 1/2003 | Mazzocchi et al. |
| 6,527,919 | B1 | 3/2003 | Roth |
| 6,547,804 | B2 | 4/2003 | Porter et al. |
| 6,551,303 | B1 | 4/2003 | Van Tassel et al. |
| 6,569,179 | B2 | 5/2003 | Teoh |
| 6,569,190 | B2 | 5/2003 | Whalen, II et al. |
| 6,572,628 | B2 | 6/2003 | Dominguez |
| 6,589,230 | B2 | 7/2003 | Gia et al. |
| 6,589,256 | B2 | 7/2003 | Forber |
| 6,605,102 | B1 | 8/2003 | Mazzocchi et al. |
| 6,620,152 | B2 | 9/2003 | Guglielmi |
| 6,669,719 | B2 | 12/2003 | Wallace et al. |
| 6,689,159 | B2 | 2/2004 | Lau et al. |
| 6,746,468 | B1 | 6/2004 | Sepetka |
| 6,780,196 | B2 | 8/2004 | Chin et al. |
| 6,802,851 | B2 | 10/2004 | Jones |
| 6,811,560 | B2 | 11/2004 | Jones |
| 6,833,003 | B2 | 12/2004 | Jones et al. |
| 6,846,316 | B2 | 1/2005 | Abrams |
| 6,849,081 | B2 | 2/2005 | Sepetka et al. |
| 6,855,154 | B2 | 2/2005 | Abdel-Gawwad |
| 6,949,116 | B2 | 9/2005 | Solymar et al. |
| 6,964,657 | B2 | 11/2005 | Cragg et al. |
| 6,964,671 | B2 | 11/2005 | Cheng |
| 6,994,711 | B2 | 2/2006 | Hieshima et al. |
| 7,044,134 | B2 | 5/2006 | Khairkhahan et al. |
| 7,083,632 | B2 | 8/2006 | Avellanet |
| 7,093,527 | B2 | 8/2006 | Rapaport et al. |
| 7,128,736 | B1 | 10/2006 | Abrams et al. |
| 7,152,605 | B2 | 12/2006 | Khairkhahan et al. |
| 7,153,323 | B1 | 12/2006 | Teoh |
| 7,195,636 | B2 | 3/2007 | Avellanet et al. |
| 7,229,454 | B2 | 6/2007 | Tran et al. |
| 7,229,461 | B2 | 6/2007 | Chin et al. |
| 7,309,345 | B2 | 12/2007 | Wallace |
| 7,371,249 | B2 | 5/2008 | Douk et al. |
| 7,377,932 | B2 | 5/2008 | Mitelberg et al. |
| 7,410,482 | B2 | 8/2008 | Murphy et al. |
| 7,572,288 | B2 | 8/2009 | Cox |
| 7,597,704 | B2 | 10/2009 | Frazier et al. |
| 7,608,088 | B2 | 10/2009 | Jones |
| 7,695,488 | B2 | 4/2010 | Berenstein et al. |
| 7,713,264 | B2 | 5/2010 | Murphy |
| 7,744,652 | B2 | 6/2010 | Morsi |
| 7,892,248 | B2 | 2/2011 | Tran |
| 7,985,238 | B2 | 7/2011 | Balgobin et al. |
| RE42,758 | E | 9/2011 | Ken |
| 8,016,852 | B2 | 9/2011 | Ho |
| 8,021,416 | B2 | 9/2011 | Abrams |
| 8,025,668 | B2 | 9/2011 | McCartney |
| 8,034,061 | B2 | 10/2011 | Amplatz et al. |
| 8,048,145 | B2 | 11/2011 | Evans et al. |
| 8,062,325 | B2 | 11/2011 | Mitelberg et al. |
| 8,075,585 | B2 | 12/2011 | Lee et al. |
| 8,142,456 | B2 | 3/2012 | Rosqueta et al. |
| 8,221,483 | B2 | 7/2012 | Ford et al. |
| 8,261,648 | B1 | 9/2012 | Marchand et al. |
| 8,267,923 | B2 | 9/2012 | Murphy |
| 8,361,106 | B2 | 1/2013 | Solar et al. |
| 8,361,138 | B2 | 1/2013 | Adams |
| 8,372,114 | B2 | 2/2013 | Hines |
| 8,398,671 | B2 | 3/2013 | Chen |
| 8,430,012 | B1 | 4/2013 | Marchand |
| 8,454,633 | B2 | 6/2013 | Amplatz et al. |
| 8,523,897 | B2 | 9/2013 | van der Burg et al. |
| 8,523,902 | B2 | 9/2013 | Heaven et al. |
| 8,551,132 | B2 | 10/2013 | Eskridge et al. |
| 8,777,974 | B2 | 7/2014 | Amplatz et al. |
| 8,900,304 | B1 | 12/2014 | Alobaid |
| 8,974,512 | B2 | 3/2015 | Aboytes et al. |
| 8,992,568 | B2 | 3/2015 | Duggal et al. |
| 8,998,947 | B2 | 4/2015 | Aboytes et al. |
| 9,055,948 | B2 | 6/2015 | Jaeger et al. |
| 9,107,670 | B2 | 8/2015 | Hannes et al. |
| 9,161,758 | B2 | 10/2015 | Figulla et al. |
| 9,232,992 | B2 | 1/2016 | Heidner et al. |
| 9,259,337 | B2 | 2/2016 | Cox et al. |
| 9,314,326 | B2 | 4/2016 | Wallace et al. |
| 9,351,715 | B2 | 5/2016 | Mach |
| 9,414,842 | B2 | 8/2016 | Glimsdale et al. |
| 9,526,813 | B2 | 12/2016 | Cohn et al. |
| 9,532,792 | B2 | 1/2017 | Galdonik et al. |
| 9,532,873 | B2 | 1/2017 | Kelley |
| 9,533,344 | B2 | 1/2017 | Monetti et al. |
| 9,539,011 | B2 | 1/2017 | Chen et al. |
| 9,539,022 | B2 | 1/2017 | Bowman |
| 9,539,122 | B2 | 1/2017 | Burke et al. |
| 9,539,382 | B2 | 1/2017 | Nelson |
| 9,549,830 | B2 | 1/2017 | Bruszewski et al. |
| 9,554,805 | B2 | 1/2017 | Tompkins et al. |
| 9,561,096 | B2 | 2/2017 | Kim et al. |
| 9,561,125 | B2 | 2/2017 | Bowman et al. |
| 9,572,982 | B2 | 2/2017 | Burnes et al. |
| 9,579,104 | B2 | 2/2017 | Beckham et al. |
| 9,579,484 | B2 | 2/2017 | Barnell |
| 9,585,642 | B2 | 3/2017 | Dinsmoor et al. |
| 9,585,669 | B2 | 3/2017 | Becking et al. |
| 9,615,832 | B2 | 4/2017 | Bose et al. |

(56) References Cited

U.S. PATENT DOCUMENTS

| | | |
|---|---|---|
| 9,615,951 B2 | 4/2017 | Bennett et al. |
| 9,622,753 B2 | 4/2017 | Cox |
| 9,629,635 B2 | 4/2017 | Hewitt et al. |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,681,861 B2 | 6/2017 | Heisel et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,826,980 B2 | 11/2017 | Figulla et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,720 B2 | 3/2018 | Marchand et al. |
| 9,955,976 B2 | 5/2018 | Hewitt et al. |
| 10,004,510 B2 | 6/2018 | Gerberding |
| 10,130,372 B2 | 11/2018 | Griffin |
| 10,307,148 B2 | 6/2019 | Heisel et al. |
| 10,327,781 B2 | 6/2019 | Divino et al. |
| 10,342,546 B2 | 7/2019 | Sepetka et al. |
| 10,517,604 B2 | 12/2019 | Bowman et al. |
| 10,653,425 B1 | 5/2020 | Gorochow et al. |
| 10,716,573 B2 | 7/2020 | Connor |
| 10,743,884 B2 | 8/2020 | Lorenzo |
| 10,751,066 B2 | 8/2020 | Lorenzo |
| 11,464,518 B2 | 10/2022 | Connor |
| 2002/0068974 A1 | 6/2002 | Kuslich et al. |
| 2002/0082638 A1 | 6/2002 | Porter et al. |
| 2002/0143349 A1 | 10/2002 | Gifford, III et al. |
| 2002/0147497 A1 | 10/2002 | Belef et al. |
| 2002/0188314 A1 | 12/2002 | Anderson et al. |
| 2003/0028209 A1 | 2/2003 | Teoh et al. |
| 2003/0120337 A1 | 6/2003 | Van Tassel et al. |
| 2003/0171739 A1 | 9/2003 | Murphy et al. |
| 2003/0176884 A1 | 9/2003 | Berrada et al. |
| 2003/0181927 A1 | 9/2003 | Wallace |
| 2003/0181945 A1 | 9/2003 | Opolski |
| 2003/0195553 A1 | 10/2003 | Wallace |
| 2003/0216772 A1 | 11/2003 | Konya |
| 2004/0034366 A1 | 2/2004 | van der Burg et al. |
| 2004/0034386 A1 | 2/2004 | Fulton et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | Van Tassel et al. |
| 2004/0133222 A1 | 7/2004 | Tran et al. |
| 2004/0153120 A1 | 8/2004 | Seifert et al. |
| 2004/0210297 A1 | 10/2004 | Lin et al. |
| 2004/0254594 A1 | 12/2004 | Alfaro |
| 2005/0021016 A1 | 1/2005 | Malecki et al. |
| 2005/0021072 A1 | 1/2005 | Wallace |
| 2005/0159771 A1 | 7/2005 | Petersen |
| 2005/0177103 A1 | 8/2005 | Hunter et al. |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Guterman et al. |
| 2006/0106421 A1 | 5/2006 | Teoh |
| 2006/0155323 A1 | 7/2006 | Porter et al. |
| 2006/0155367 A1 | 7/2006 | Hines |
| 2006/0167494 A1 | 7/2006 | Suddaby |
| 2006/0247572 A1 | 11/2006 | McCartney |
| 2007/0088387 A1 | 4/2007 | Eskridge et al. |
| 2007/0106311 A1 | 5/2007 | Wallace et al. |
| 2007/0208376 A1 | 6/2007 | Meng |
| 2007/0162071 A1 | 7/2007 | Burkett et al. |
| 2007/0167876 A1 | 7/2007 | Euteneuer et al. |
| 2007/0173928 A1 | 7/2007 | Morsi |
| 2007/0186933 A1 | 8/2007 | Domingo |
| 2007/0191884 A1 | 8/2007 | Eskridge et al. |
| 2007/0233188 A1 | 10/2007 | Hunt et al. |
| 2007/0265656 A1 | 11/2007 | Amplatz et al. |
| 2007/0288083 A1 | 12/2007 | Hines |
| 2008/0097495 A1 | 4/2008 | Feller, III et al. |
| 2008/0103505 A1 | 5/2008 | Fransen |
| 2008/0119886 A1 | 5/2008 | Greenhalgh et al. |
| 2008/0281350 A1 | 11/2008 | Sepetka et al. |
| 2009/0036877 A1 | 2/2009 | Nardone et al. |
| 2009/0062841 A1 | 3/2009 | Amplatz et al. |
| 2009/0099647 A1 | 4/2009 | Glimsdale |
| 2009/0227983 A1 | 9/2009 | Griffin et al. |
| 2009/0281557 A1 | 11/2009 | Sander et al. |
| 2009/0287291 A1 | 11/2009 | Becking et al. |
| 2009/0287294 A1 | 11/2009 | Rosqueta et al. |
| 2009/0287297 A1 | 11/2009 | Cox |
| 2009/0318941 A1 | 12/2009 | Sepetka |
| 2010/0023046 A1 | 1/2010 | Heidner et al. |
| 2010/0023048 A1 | 1/2010 | Mach |
| 2010/0063573 A1 | 3/2010 | Hijlkema |
| 2010/0063582 A1 | 3/2010 | Rudakov |
| 2010/0069948 A1 | 3/2010 | Veznedaroglu et al. |
| 2010/0168781 A1 | 7/2010 | Berenstein |
| 2010/0211156 A1 | 8/2010 | Linder et al. |
| 2010/0324649 A1 | 12/2010 | Mattsson et al. |
| 2011/0046658 A1 | 2/2011 | Conner et al. |
| 2011/0054519 A1 | 3/2011 | Neuss |
| 2011/0112588 A1 | 5/2011 | Linderman et al. |
| 2011/0137317 A1 | 6/2011 | O'Halloran et al. |
| 2011/0152993 A1 | 6/2011 | Marchand et al. |
| 2011/0196413 A1 | 8/2011 | Wallace |
| 2011/0319978 A1 | 12/2011 | Schaffer |
| 2012/0010644 A1 | 1/2012 | Sideris et al. |
| 2012/0071911 A1 | 3/2012 | Sadasivan |
| 2012/0165732 A1 | 6/2012 | Müller |
| 2012/0191123 A1 | 7/2012 | Brister et al. |
| 2012/0283768 A1 | 11/2012 | Cox et al. |
| 2012/0310270 A1 | 12/2012 | Murphy |
| 2012/0323267 A1 | 12/2012 | Ren |
| 2012/0330341 A1 | 12/2012 | Becking et al. |
| 2013/0035665 A1 | 2/2013 | Chu |
| 2013/0035712 A1 | 2/2013 | Theobald et al. |
| 2013/0066357 A1 | 3/2013 | Aboytes et al. |
| 2013/0079864 A1 | 3/2013 | Boden |
| 2013/0110066 A1 | 5/2013 | Sharma et al. |
| 2013/0204351 A1 | 8/2013 | Cox et al. |
| 2013/0211495 A1 | 8/2013 | Halden et al. |
| 2013/0261658 A1 | 10/2013 | Lorenzo et al. |
| 2013/0261730 A1 | 10/2013 | Bose et al. |
| 2013/0274863 A1 | 10/2013 | Cox et al. |
| 2013/0345738 A1 | 12/2013 | Eskridge |
| 2014/0005714 A1* | 1/2014 | Quick .............. A61B 17/12031 606/200 |
| 2014/0012307 A1 | 1/2014 | Franano et al. |
| 2014/0012363 A1 | 1/2014 | Franano et al. |
| 2014/0018838 A1 | 1/2014 | Franano et al. |

(56) References Cited

U.S. PATENT DOCUMENTS

| | | |
|---|---|---|
| 2014/0135812 A1 | 5/2014 | Divino et al. |
| 2014/0200607 A1* | 7/2014 | Sepetka .......... A61B 17/12109 606/200 |
| 2014/0257360 A1 | 9/2014 | Keillor |
| 2014/0257361 A1 | 9/2014 | Prom |
| 2014/0277013 A1 | 9/2014 | Sepetka et al. |
| 2014/0358178 A1 | 12/2014 | Hewitt et al. |
| 2015/0057703 A1* | 2/2015 | Ryan .................. A61B 17/2909 606/213 |
| 2015/0209050 A1 | 7/2015 | Aboytes et al. |
| 2015/0272589 A1 | 10/2015 | Lorenzo |
| 2015/0313605 A1 | 11/2015 | Griffin |
| 2015/0342613 A1 | 12/2015 | Aboytes et al. |
| 2015/0374483 A1* | 12/2015 | Janardhan ............... A61M 1/74 606/200 |
| 2016/0022445 A1 | 1/2016 | Ruvalcaba et al. |
| 2016/0030050 A1 | 2/2016 | Franano et al. |
| 2016/0192912 A1 | 7/2016 | Kassab et al. |
| 2016/0249934 A1 | 9/2016 | Hewitt et al. |
| 2016/0249935 A1 | 9/2016 | Hewitt et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079661 A1 | 3/2017 | Bardsley et al. |
| 2017/0079662 A1 | 3/2017 | Rhee et al. |
| 2017/0079671 A1 | 3/2017 | Morero et al. |
| 2017/0079680 A1 | 3/2017 | Bowman |
| 2017/0079717 A1 | 3/2017 | Walsh et al. |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0114350 A1 | 8/2017 | Shimizu et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0258473 A1 | 9/2017 | Plaza et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340333 A1 | 11/2017 | Badruddin et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140305 A1* | 5/2018 | Connor .................... A61F 2/90 |
| 2018/0206850 A1 | 7/2018 | Wang et al. |
| 2018/0242979 A1 | 8/2018 | Lorenzo |
| 2018/0303531 A1 | 10/2018 | Sanders et al. |
| 2018/0338767 A1 | 11/2018 | Dasnurkar et al. |
| 2019/0008522 A1 | 1/2019 | Lorenzo |
| 2019/0110796 A1 | 4/2019 | Jayaraman |
| 2019/0142567 A1 | 5/2019 | Janardhan et al. |
| 2019/0192162 A1 | 6/2019 | Lorenzo |
| 2019/0192167 A1 | 6/2019 | Lorenzo |
| 2019/0192168 A1 | 6/2019 | Lorenzo |
| 2019/0223878 A1* | 7/2019 | Lorenzo ........... A61B 17/12031 |
| 2019/0223879 A1* | 7/2019 | Jayaraman ....... A61B 17/12168 |
| 2019/0223881 A1 | 9/2019 | Hewitt et al. |
| 2019/0328398 A1 | 10/2019 | Lorenzo |
| 2019/0357914 A1* | 11/2019 | Gorochow ........ A61M 25/0021 |
| 2019/0365385 A1 | 12/2019 | Gorochow et al. |
| 2020/0000477 A1 | 1/2020 | Nita et al. |
| 2020/0069313 A1* | 3/2020 | Xu ................... A61B 17/12172 |
| 2020/0268365 A1* | 8/2020 | Hebert ............. A61B 17/12031 |
| 2020/0375606 A1 | 12/2020 | Lorenzo |
| 2021/0007755 A1 | 1/2021 | Lorenzo et al. |
| 2021/0177429 A1 | 6/2021 | Lorenzo |

FOREIGN PATENT DOCUMENTS

| | | |
|---|---|---|
| CA | 2598048 A1 | 5/2008 |
| CN | 204 683 687 U | 10/2015 |
| CN | 107374688 A | 11/2017 |
| DE | 102008015781 A1 | 10/2009 |
| DE | 102010053111 A1 | 6/2012 |
| DE | 102009058132 B4 | 7/2014 |
| DE | 10 2013 106031 A1 | 12/2014 |
| DE | 202008018523 U1 | 4/2015 |
| DE | 102011102955 B4 | 5/2018 |
| EP | 1054635 B1 | 11/2000 |
| EP | 1295563 A1 | 3/2003 |
| EP | 1441649 B1 | 8/2004 |
| EP | 1483009 B1 | 12/2004 |
| EP | 1527753 B1 | 5/2005 |
| EP | 1569565 B1 | 9/2005 |
| EP | 1574169 B1 | 9/2005 |
| EP | 1494619 B1 | 1/2006 |
| EP | 1633275 B1 | 3/2006 |
| EP | 1659988 B1 | 5/2006 |
| EP | 1725185 B1 | 11/2006 |
| EP | 1862122 A1 | 12/2007 |
| EP | 1923005 B1 | 5/2008 |
| EP | 2063791 B1 | 6/2009 |
| EP | 2134263 B1 | 12/2009 |
| EP | 2157937 B1 | 3/2010 |
| EP | 2266456 A1 | 12/2010 |
| EP | 2324775 B1 | 5/2011 |

(56) References Cited

FOREIGN PATENT DOCUMENTS

| | | |
|---|---|---|
| EP | 2367482 B1 | 9/2011 |
| EP | 2387951 B1 | 11/2011 |
| EP | 2460476 A2 | 6/2012 |
| EP | 2468349 A1 | 6/2012 |
| EP | 2543345 A1 | 1/2013 |
| EP | 2567663 A1 | 3/2013 |
| EP | 2617386 A1 | 7/2013 |
| EP | 2623039 A1 | 8/2013 |
| EP | 2647343 A2 | 10/2013 |
| EP | 2848211 A1 | 3/2015 |
| EP | 2854704 B1 | 4/2015 |
| EP | 2923674 B1 | 9/2015 |
| EP | 2926744 A1 | 10/2015 |
| EP | 3146916 A1 | 3/2017 |
| EP | 3501429 A1 | 6/2019 |
| EP | 3517055 A1 | 7/2019 |
| JP | H04-47415 U | 4/1992 |
| JP | H07-37200 U | 7/1995 |
| JP | 2006-509578 A | 3/2006 |
| JP | 2013-509972 A | 3/2013 |
| JP | 2013537069 A | 9/2013 |
| JP | 2014-522268 A | 9/2014 |
| JP | 2016-502925 A | 2/2015 |
| WO | WO 9641589 A1 | 12/1996 |
| WO | WO 9905977 A1 | 2/1999 |
| WO | WO 9908607 A1 | 2/1999 |
| WO | WO 9930640 A1 | 6/1999 |
| WO | WO 2003073961 A1 | 9/2003 |
| WO | WO 03/086240 A1 | 10/2003 |
| WO | WO 2005020822 A1 | 3/2005 |
| WO | WO 2005074814 A2 | 8/2005 |
| WO | 2005117718 A1 | 12/2005 |
| WO | WO 2006034149 A2 | 3/2006 |
| WO | WO 2006052322 A2 | 5/2006 |
| WO | 2007/076480 A2 | 7/2007 |
| WO | WO 2008150346 A1 | 12/2008 |
| WO | WO 2008151204 A1 | 12/2008 |
| WO | WO 2009048700 A1 | 4/2009 |
| WO | WO 2009105365 A1 | 8/2009 |
| WO | WO 2009132045 A2 | 10/2009 |
| WO | WO 2009135166 A2 | 11/2009 |
| WO | WO 2010030991 A1 | 3/2010 |
| WO | WO 2011057002 A2 | 5/2011 |
| WO | WO 2012032030 A1 | 3/2012 |
| WO | WO-2012034135 A1 * | 3/2012 ....... A61B 17/12031 |
| WO | WO 2012099704 A2 | 7/2012 |
| WO | WO 2012099909 A2 | 7/2012 |
| WO | WO 2012113554 A1 | 8/2012 |
| WO | WO 2013016618 A2 | 1/2013 |
| WO | WO 2013025711 A1 | 2/2013 |
| WO | WO 2013109309 A1 | 7/2013 |
| WO | WO 2013159065 A1 | 10/2013 |
| WO | WO 2013162817 A1 | 10/2013 |
| WO | WO 2014029835 A1 | 2/2014 |
| WO | WO 2014078286 A1 | 5/2014 |
| WO | WO 2014110589 A1 | 7/2014 |
| WO | WO 2014137467 A1 | 9/2014 |
| WO | WO 2015073704 A1 | 5/2015 |
| WO | 2015160721 A1 | 10/2015 |
| WO | 2015171268 A2 | 11/2015 |
| WO | WO 2015166013 A1 | 11/2015 |
| WO | WO 2015184075 A1 | 12/2015 |
| WO | WO 2015187196 A1 | 12/2015 |
| WO | WO 2016044647 A2 | 3/2016 |
| WO | WO 2016107357 A1 | 7/2016 |
| WO | WO 2016137997 A1 | 9/2016 |
| WO | WO 2017/161283 A1 | 9/2017 |
| WO | WO 2018051187 A1 | 3/2018 |
| WO | WO 2019/038293 A1 | 2/2019 |

OTHER PUBLICATIONS

Extended European Search Report issued in corresponding European Patent Application No. 19 21 5277 dated May 12, 2020.

Altes et al., Creation of Saccular Aneurysms in the Rabbit: A Model Suitable for Testing Endovascular Devices. AJR 2000; 174: 349-354.

Schaffer, Advanced Materials & Processes, Oct. 2002, pp. 51-54.

* cited by examiner

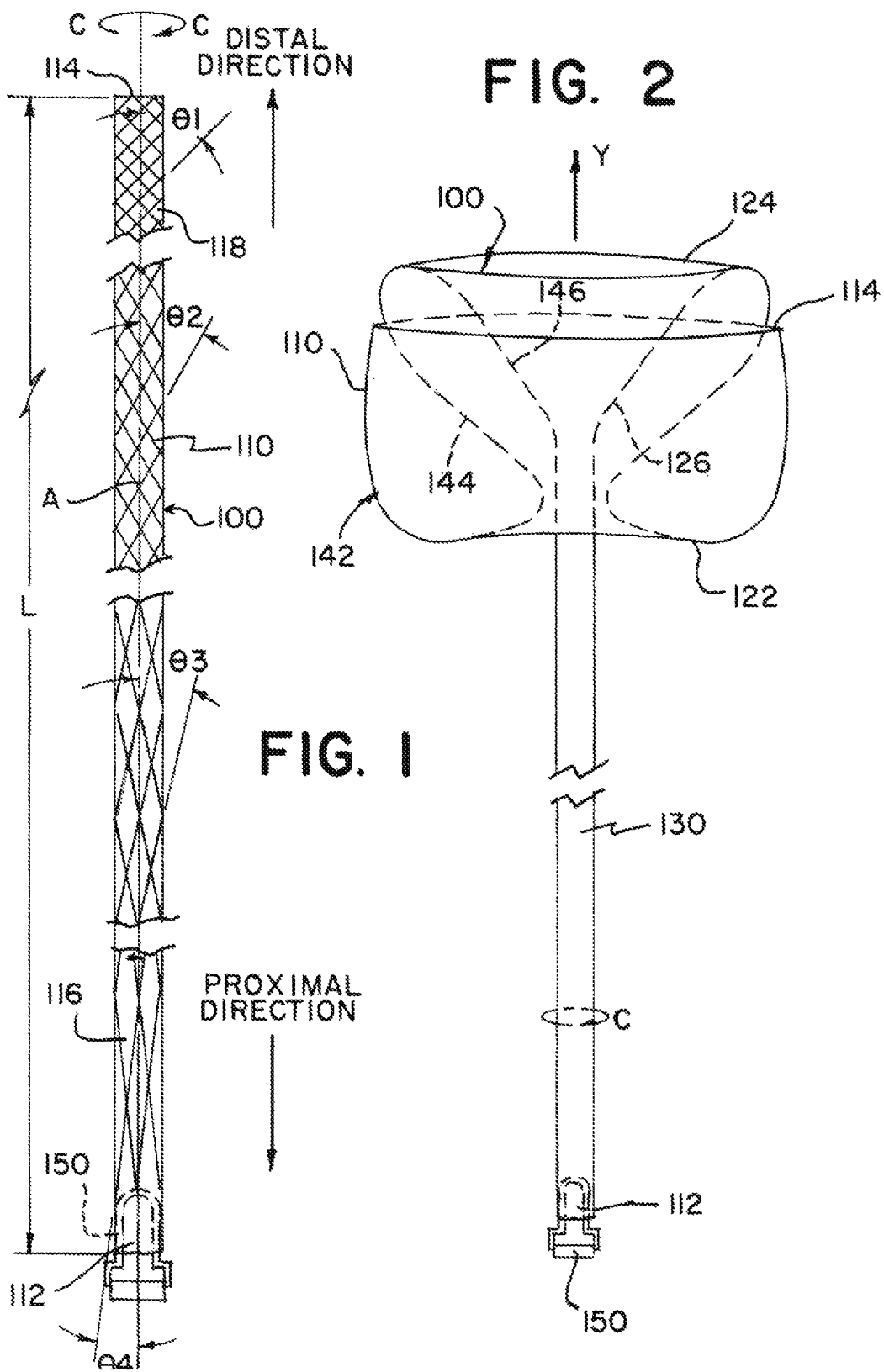

INTRASACCULAR INVERTING BRAID WITH HIGHLY FLEXIBLE FILL MATERIAL

FIELD OF INVENTION

The present invention generally relates to medical instruments, and more particularly, to embolic implants for aneurysm therapy.

BACKGROUND

Cranial aneurysms can be complicated and difficult to treat due to their proximity to critical brain tissues. Prior solutions have included endovascular treatment whereby an internal volume of the aneurysm sac is removed or excluded from arterial blood pressure and flow. Current alternatives to endovascular or other surgical approaches can include intravascularly delivered treatment devices that fill the sac of the aneurysm with embolic material or block the entrance or neck of the aneurysm. Both approaches attempt to prevent blood flow into the aneurysm. When filling an aneurysm sac, the embolic material clots the blood, creating a thrombotic mass within the aneurysm. When treating the aneurysm neck, blood flow into the entrance of the aneurysm is inhibited, inducing venous stasis in the aneurysm and facilitating a natural formation of a thrombotic mass within the aneurysm.

Current intravascularly delivered devices typically utilize multiple embolic coils to either fill the sac or treat the entrance of the aneurysm. Naturally formed thrombotic masses formed by treating the entrance with embolic coils can result in improved healing compared to aneurysm masses packed with embolic coils because naturally formed thrombotic masses can reduce the likelihood of distention from arterial walls and facilitate reintegration into the original parent vessel shape along the neck plane. However, embolic coils delivered to the neck of the aneurysm can potentially have the adverse effect of impeding the flow of blood in the adjoining blood vessel, particularly if the entrance is overpacked. Conversely, if the entrance is insufficiently packed, blood flow can persist into the aneurysm. Treating certain aneurysm morphology (e.g. wide neck, bifurcation, etc.) can require ancillary devices such a stents or balloons to support the coil mass and obtain the desired packing density. Once implanted, the coils cannot easily be retracted or repositioned. Furthermore, embolic coils do not always effectively treat aneurysms as aneurysms treated with multiple coils often recanalize or compact because of poor coiling, lack of coverage across the aneurysm neck, blood flow, or large aneurysm size.

Alternatives to embolic coils are being explored, for example a tubular braided implant is disclosed in U.S. Patent Publication Number 2018/0242979, incorporated herein by reference. Tubular braided implants have the potential to easily, accurately, and safely treat an aneurysm or other arterio-venous malformation in a parent vessel without blocking flow into perforator vessels communicating with the parent vessel. Compared to embolic coils, however, tubular braided implants are a newer technology, and there is therefore capacity for improved geometries, configurations, delivery systems, etc. for the tubular braided implants.

There is therefore a need for improved methods, devices, and systems for implants for aneurysm treatment.

SUMMARY

It is an object of the present invention to provide systems, devices, and methods to meet the above-stated needs. Generally, it is an object of the present invention to provide a tubular braided implant including a braid that can be delivered as a single layer braid, can invert into itself during deployment to form at least two nested sacks, and can include additional braid material that can fill the innermost sack. The additional braid material can loop or coil like a ribbon and/or invert to form smaller and smaller nested sacks. In order to have an implant that can invert and fill an aneurysm, the braid can be made such that the distal end, the braid is made stronger, having a tendency to move toward a predetermined shape when implanted and forming the two nested sacks, and at the proximal end, the braid can be made weaker, having a tendency to flatten and fold in a ribbon shape inside of the sacks. The braid can have a variable braid angle along its length such that when positioned for delivery, the braid can have a high braid angle near its distal end and a low braid angle near the proximal end. In addition to the variable braid angle, or as an alternative, the braid can be heat treated to weaken the braid at the proximal end. In addition, or as a replacement for the braid material that fills the innermost sack, the implant can include an embolic coil that can loop within the innermost sack.

An example method for treating an aneurysm can include one or more of the following steps presented in no particular order. The example method can further include additional steps not listed here. A substantially tubular braid can be selected that has a first end, a second end, a first portion extending from the first end, and a second portion extending from the second end. The substantially tubular braid can be selected such that the braid, when in a single layer cylindrical shape having a uniform circumference along a length from one end of the braid to the other end of the braid, the braid has a smaller braid angle in the second portion of the braid compared to the first portion of the braid. The braid can be selected such that, when in the single layer cylindrical shape, the braid has a continuously decreasing braid angle extending from the first portion to the second portion.

The braid can be delivered through a microcatheter to an aneurysm. The braid can be delivered in the single layer tubular shape such that the first end is positioned in the distal direction in relation to the second end.

The first portion of the braid can be expanded to the aneurysm's wall. A proximal inversion can be formed in the braid at the aneurysm's neck. An inverted portion of the braid can be expanded to press into the expanded first portion. A distal inversion can be formed in the braid at a distal portion of the aneurysm's wall such that the inverted portion of the braid extends between the distal and proximal inversions.

The braid can be shaped to form a dome near the distal portion of the aneurysm's wall within the inverted portion. Additionally, or alternatively, the braid can be twisted at the distal inversion and the braid can be expanded to form a sack within the inverted portion.

The second portion of the braid can be positioned within the inverted portion, either directly in contact with the inverted portion, within sacks formed within the inverted portion, or otherwise positioned in the inverted portion. The second portion of the braid can be positioned such that the second portion is flattened and looped within the inverted portion.

An embolic coil can be selected. The embolic coil can be positioned such that it is affixed to the second end of the braid. The embolic coil can be delivered through the microcatheter to the aneurysm. The embolic coil can be positioned within the inverted portion of the implanted braid.

An example implant can include a tubular braid with two ends that is shapeable to a single layer cylindrical shape having a length measurable from one end to the other end, a substantially uniform circumference along the length, a larger braid angle on a first portion of the braid extending from a first of the two ends, and a smaller braid angel on a second portion of the braid extending from a second of the two ends. In the single layer cylindrical shape, the braid can have a continuously decreasing braid angle extending from the first portion to the second portion. In the single layer tubular shape, the braid can be sized to be delivered through a microcatheter to an aneurysm.

The braid can be movable from the single layer cylindrical shape to an implanted shape. In the implanted shape, the first portion can be positioned to appose an aneurysm wall, an inverted sack can be positioned to press the first portion to the aneurysm wall, and the second portion can be positioned within the inverted sack. In the implanted shape, at least a portion of the second portion of the braid can be looped within the inverted portion. In the implanted shape, the second portion can be positioned to press the inverted portion to the first portion.

In the implanted shape, an inner sack can be positioned to press the inverted sack to the first portion, the braid can have an inversion separating the inner sack and the inverted sack, and the braid can be twisted at the inversion.

In the implanted shape, the braid can have a dome shape within the inverted sack positioned near a distal portion of the aneurysm's wall.

The implant can further include an embolic coil affixed to the second end of the braid. In the implanted shape, the braid can be shaped to allow the embolic coil to be positioned within the inverted sack, either in direct contact with the inverted sack, separated from the inverted sack by braid material, or otherwise positioned in the inverted sack.

Another example implant can include a tubular braid having a first end and a second end. The braid can have a predetermined shape having two inversions dividing the braid into three segments: an outer segment extending from the first end to a first inversion of the two inversions, a middle segment extending between the two inversions and at least partially surrounded by the outer segment, and an inner segment extending from the second of the two inversions to the second end and at least partially surrounded by the middle segment. In the predetermined shape, the braid can have an abrupt change in braid angle at a position on the inner segment such that a distal portion of the inner segment extending from the second inversion has a higher braid angle than a proximal portion of the inner segment extending from the second end.

The braid can be movable to an implanted shape sized to be positioned within an aneurysm sac. In the implanted shape, a part of the braid corresponding to the inner segment in the predetermined shape can be collapsed to a ribbon shape and positioned in an inverted sack formed from a part of the braid corresponding to the middle segment in the predetermined shape.

The braid can be shaped to a single layer cylindrical shape having a substantially uniform circumference between the two ends of the braid, a larger braid angle in a first portion of the braid extending from the first end, and a smaller braid angle in a second portion of the braid extending from the second end. In the single layer cylindrical shape, the braid can have a continuously decreasing braid angle from the first portion to the second portion. In the single layer cylindrical shape, the braid can be sized to be delivered through a microcatheter to an aneurysm.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1 is an illustration of an implant having a braid shaped for delivery through a catheter according to aspects of the present invention;

FIG. 2 is an illustration of an implant having a braid in a predetermined shape according to aspects of the present invention;

DETAILED DESCRIPTION

Figure 3A:
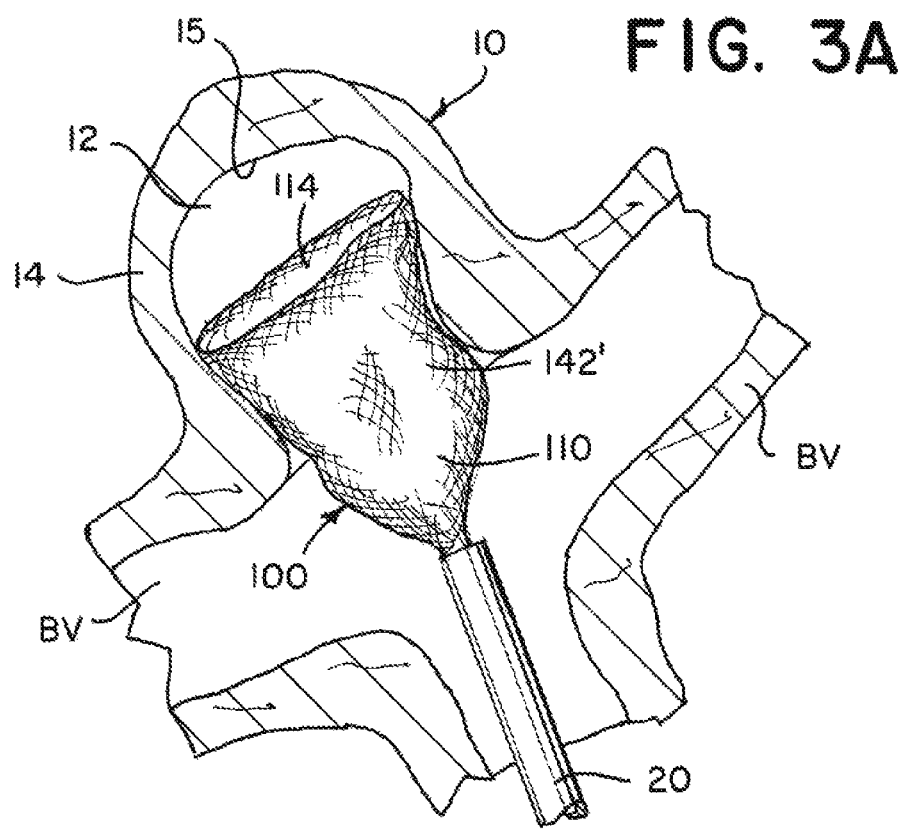
FIGS. 3A through 3I are illustrations of steps of an aneurysm treatment process according to aspects of the present invention.

In known treatments of wide neck aneurysms, the aneurysm is typically treated by placing embolic coils within the aneurysm sac and placing a stent within the parent blood vessel across the aneurysm neck. The stent is necessary in many cases to inhibit the embolic coils from entering the parent blood vessel. If embolic coils enter the parent blood vessel, the coils can obstruct the vessel and/or clots can form on the coils within the blood vessel and create an obstruction in the parent blood vessel. Braided aneurysm intrasaccular implants can be used to treat wide neck aneurysms without requiring a stent to secure the braided implant at the aneurysm neck. However, to achieve the forces necessarily to anchor braided implants in a wide neck bifurcation, the braid can be stiff and resistant to reshaping to an implanted shape that is significantly different than a predetermined shape. It can therefore be challenging, in some cases, to pack the aneurysm with a sufficient braid density to quickly and effectively induce blood stasis within the aneurysm sac. A braid made too soft can compact in shape and cause the aneurysm to recanalize as the implant is no longer sealing the neck of the aneurysm.

Aspects of the present invention are directed to address the above challenges. In examples presented herein, a tubular braided implant can include a braid that can be delivered as a single layer braid, can invert into itself during deployment to form at least two nested sacks, and can include additional braid material that can fill the innermost sack. The additional braid material can loop or coil like a ribbon and/or invert to form smaller and smaller nested sacks. An aspect of the present invention is to provide a structure that allows a sufficient amount of additional braid material to be placed into the innermost sack such that the aneurysm clots quickly for an effective treatment.

When used herein, the terms "tubular" and "tube" are to be construed broadly and are not limited to a structure that is a right cylinder or strictly circumferential in cross-section or of a uniform cross-section throughout its length. For simplicity, tubular structures are generally illustrated herein as having a substantially right cylindrical structure. However, a tubular structure can have a tapered or curved outer surface without departing from the scope of the present invention.

To meet the competing needs for braid stiffness to achieve secure anchoring within the aneurysm and braid softness to deform the braid to a high packing density within the aneurysm, the braid can be made such that portions of the braid pushed into the aneurysm when the aneurysm has a higher packing density are weaker compared to stiffer portions of the braid that expand to anchor the braid within the aneurysm. Stiffness/flexibility of the braid portions can be controlled by braid angle (e.g. picks per inch), strand diameter, number of strands, material of strands, and/or treatment (e.g. heat treatment) to modify strand material properties, etc. A stiffer portion can have a higher braid angle, a larger strand diameter, more strands, strands comprising a stiffer material, and/or strands treated to have greater stiffness compared to a weaker portion.

Stiffer portions of the braid can be positioned near a distal end of the braid when the braid is being delivered through a catheter so that the stiffer portions of the braid exit the catheter and expand to anchor in the aneurysm before the aneurysm is packed. Stiffer portions of the braid can be shaped in a predetermined shape by heat setting or other means such that when the stiffer portions, they expand toward the predetermined shape. The tendency of the stiffer portions of the braid to expand toward the predetermined shape can create sufficient force against the aneurysm walls to anchor the braid in the aneurysm sac. Weaker portions of the braid can be positioned near the proximal end of the braid when the braid is delivered through the catheter. Portions of the braid which have the most flexibility can be dynamically deformed to loop or nest within the aneurysm, folding within the stiffer, anchoring portions of braid.

In addition, or as a replacement for the braid material that fills the innermost sack, the implant can include an embolic coil that can loop within the innermost sack.

Examples presented herein generally include a braided implant that can secure within an aneurysm sac and occlude a majority of the aneurysm's neck. The implant can include a tubular braid having a stiffer portion and a weaker portion, at least the stiffer portion being set into a predetermined shape, the braid being compressible for delivery through a microcatheter, and the braid being implantable in an implanted position that is based on the geometry of the aneurysm in which the braid is implanted and based at least in part on the predetermined shape.

An example implant 100, as illustrated in FIG. 1 can include a braid 110 that can be shaped into a substantially tubular, single layer shape having a length L measured between each end 112, 114 and a variable stiffness along the length L. As illustrated, stiffness can be determined at least in part by braid angle $\theta 1, \theta 2, \theta 3, \theta 4$. For ease of discussion, weaker, more flexible portions of braid are illustrated as having a lower braid angle compared to stronger, stiffer portions of the braid; however, weaker and stiffer portions of the braids can differ in strand diameter, number of strands, material of strands, be treated to have differing stiffness/flexibility, and/or by other means as would be appreciated and understood by a person of ordinary skill in the art. Further, example implants comprising braid segments of differing stiffness can include two separate sections joined to form a braid, and the braid need not include the segments of differing stiffness as a contiguous braided tube.

In the single layer tubular shape illustrated in FIG. 1, the braid 110 can have a circumference C that is substantially uniform along the length L. The tubular shape can have a central axis A extending along the length of the braid 110. A braid angle $\theta 1, \theta 2, \theta 3, \theta 4$ can be measured by comparing the tangential trajectory of a braid strand to the central axis A as illustrated and as would otherwise be understood by a person of ordinary skill in the art according to the teachings herein.

The braid can include a number of strands, for example, from about 4 to about 96 strands, each extending from one braid end 112 to the other 114. As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%. The strands can wrap helically around the circumference C. The number of strands, angle of strands, diameter of the strands, material of strands, and material properties of strands, can all be factors in controlling material properties of the braid 110, including porosity and flexibility. Braid strands can be woven such that about half of the strands wrap in a clockwise helix, the other half wraps in a counterclockwise helix, and the oppositely wrapping strands cross over and under each other in an alternating fashion. Constructed as such, portions of the braid having a higher braid angle can therefore having a higher density of strands compared to portions of the braid having lower braid angle. Higher strand density can result in a denser, stiffer braid portion.

The strands can be made from multiple alloys such as a nickel-titanium alloy, cobalt chromium alloys, platinum, nitinol, stainless steel, tantalum, or other alloys, or any other suitable biocompatible materials, or combination of these materials. Also, these materials can be absorbable or non-absorbable by the patient over time. Some or all of braid 110 can be a multi-filament cylindrical mesh made preferably of nitinol with interwoven platinum filaments for radiopacity or Drawn Filled Tube (DFT) Nitinol with about 10 to about 40% platinum. The apertures in the mesh of braid 110 can also create a substantially unitary frame work or mesh. Thus, the apertures can have variable size, shape, or porosity, and may be uniformly or randomly spaced throughout the wall of the mesh of braid 110. The apertures can provide the braid 110 with flexibility and also assist in the transformation of the braid from the collapsed state to the expanded, deployed state, and vice versa.

The braid 110 as illustrated in FIG. 1 depicts four braid angles $\theta 1, \theta 2, \theta 3, \theta 4$ that increase as measured from the proximal end 112 of the braid 110 to the distal end 114 with the braid angle $\theta 4$ in the proximal portion 116 of the braid 110 being the smallest, the braid angle $\theta 3$ in the section immediate distal to the proximal portion 116 being larger than the braid angle $\theta 4$ in the proximal portion 116, the braid angle $\theta 2$ in the next distal section being larger than the angle $\theta 3$ in the section immediately proximal to it, and the braid angle $\theta 1$ in the distal most section 118 of the braid 110 being the largest. As would be appreciated and understood, the braid 110 can include two or more sections having differing braid angles and thereby differing stiffness/flexibility. The braid can additionally include a continuous gradient change in braid angle and thereby continuous gradient change in stiffness/flexibility from one braid section to another, for instance the braid angle can change continuously from the proximal portion 116 to the distal portion 118.

The implant 100 can be delivered to an aneurysm when the braid 110 is sized to traverse a catheter. For instance, the braid 110 can be delivered in the single-layer tubular shape as illustrated in FIG. 1 such that one end of the braid 114 is a distal end positioned to exit the catheter before the remainder of the braid 110 and the other end 112 is a proximal end positioned to exit the catheter after the remainder of the braid 110. Alternatively, the braid can be delivered in other shapes that include folds, inversions, and/or multiple layers. Regardless of the delivery shape, the braid 110 can have a distal portion 118 positioned to exit the catheter before the remainder of the braid 110 and a proximal portion 116 positioned to exit the catheter after the remainder of the braid 110. The distal portion 118 can have a high braid angle θ1 such that the distal portion 118 has sufficient stiffness to anchor the braid 110 within the aneurysm. The proximal portion 116 can have a low braid angle θ4 such that the proximal portion has sufficient flexibility to collapse into an aneurysm sac containing the remainder of braid 110. The implant 100 can further include a detachment feature 150 configured to be detachably attached to an implant delivery system. The detachment feature 150 can be affixed to the braid 110 at the proximal end 112 of the braid 110.

FIG. 2 illustrates a braid 110 such as the braid 110 illustrated in FIG. 1 shaped into a predetermined shape. The braid 110 can include a memory shape material such as Nitinol, a Nitinol alloy, a polymer memory shape material, or other memory shape material having properties for reshaping as described herein. The braid 110 can be set to the predetermined shape by heat setting or other means as appreciated and understood by a person of ordinary skill in the art. The braided segment 110 can be collapsed from the predetermined shape to a deformed shape sized to traverse a microcatheter to an aneurysm. Upon contact with blood when exiting the microcatheter, the braid 110 can move from the deformed shape toward the predetermined shape. The anatomy of the aneurysm and treatment site can inhibit the braid 110 from moving to the predetermined shape such that when the braid 110 is deployed, it can take on a deployed shape that is based in part on the predetermined shape and the shape of the anatomy in which the braid is implanted.

In the predetermined shape, the braid 110 can include two inversions 122, 124 and a pinch point 126 dividing the braid 110 into four segments 142, 144, 146, 130. In the predetermined shape, the braid 110 can have an outer segment 142 extending from the open end 114 of the braid 110 to a first inversion 122 of the two inversions 122, 124, a middle segment 144 extending between the two inversions 122, 124, an inner segment 146 extending from a second inversion 124 of the two inversions 122, 124 to the pinched point 126 of the braid 110, and an elongated section 130 extending from the pinch point 126 to an opposite end 112 of the braid 110. When in the predetermined shape, the tubular braid 110 can be substantially radially symmetrical around a central vertical axis y.

FIG. 2 illustrates a profile of each segment 142, 144, 146, 130. The detachment feature 150 is illustrated as a flat key that can be used with a mechanical implant delivery system (not illustrated). Example implant delivery systems are described, for instance, in U.S. Patent Application Publication Numbers 2019/0192162 and 2019/0328398 each incorporated herein by reference as if set for in their entireties herein. During delivery and/or positioning of the implant, the key 150 can be visualized radiographically. The key 150 can be released from the delivery system, thereby releasing the implant 100 from the delivery system. When the implant is released, the key can remain attached to the implant.

The tubular braid 110 can be formed into the predetermined shape by first pinching the braid 110 at the pinch point 126, then inverting the braid outwardly to separate the inner segment 146 from the middle segment 144 with an inversion 124, then shaping the middle segment 144 over a form to produce the substantially "S" shaped profile illustrated, and finally, inverting the braid 110 outwardly again to separate the middle segment 144 from the outer segment 142 with another inversion 122. Optionally, the braid can be trimmed at the open end 114 and/or the proximal end 112. The open end 114 can be positioned to encircle the middle segment 144. The open end 114 can positioned within the middle third section of the braid's height as illustrated. Alternatively, the open end 114 can be positioned elsewhere, such as near the distal inversion 124.

The outer sack 142 can correspond to the distal portion 118 of the braid 110 as illustrated in FIG. 1. The distal portion 118 can have a substantially uniform braid angle θ1 along its length when the single layer tubular shape illustrated in FIG. 1 The braid 110 can have an abrupt braid angle change at the proximal inflection 122. The braid 110 can have a graduated braid angle change through the middle section 144 and inner section 146. The tail 130 can have a braid angle θ4 that is substantially consistent along the length of the tail 130. The tail 130 can correspond to the proximal portion 116 of the braid 110 in the single layer tubular shape as illustrated in FIG. 1.

Alternatively, sections 142, 144, 146 distal to the pinch point 126 can have a high braid angle θ1 that is consistent along the length of those sections 142, 144, 146 when the braid 110 is in a single layer tubular shape, the tail section 130 can have a low braid angle θ4 consistent along its length, and the braid 110 can have an abrupt change in braid angle at the pinch point 126. The tail 130 can be sufficiently flexible such that, when manipulated at an intravascular treatment site, it flattens to a ribbon shape and folds onto itself. Alternatively, braid 110 can include an abrupt braid angle change at the proximal inflection 122, at the distal inflection 124, at the pinch point 126, or any combination thereof.

Strands of the braid 110 at the open end 114 can be free, cut ends; or, alternatively, the strands at the open end 114 be closed, meaning strands within the braid at the open end 114 are attached to each other by glue, weld, etc. or the strands bend back at the open end 114. Free cut ends can have an advantage of being easier to manufacture while the closed strand ends can have an advantage of being more atraumatic compared to the cut ends.

FIGS. 3A through 3I illustrate an implant 100 such as the implant 100 illustrated in FIGS. 1 and/or 2 being implant in an aneurysm 10 via a catheter 20. The size of the catheter 20 can be selected in consideration of the size, shape, and directionality of the aneurysm or the body lumens the catheter must pass through to get to the treatment site. The catheter 20 can have a total usable length from about 80 centimeters to about 170 centimeters. The catheter 20 can have an inner diameter ID of from about 0.015 to about 0.032 inches. The outer diameter OD can also range in size and may narrow at either its proximal end or distal end. At its proximal end 26, the catheter 20 can be manually operated by the end-user, and at its distal end can be operable, as illustrated, to be positioned at the neck 16 of the aneurysm 10. While the distal end of the catheter 20 can contain the implant 100, the distal end can be varied in shape and can curve at an angle.

FIG. 3A illustrates the open end 114 of the braid 110 expanding within a sac 12 of the aneurysm 10 to contact walls 14 of the aneurysm 10. The section 142' contacting the aneurysm wall 14 can correspond to the outer 142 section in the predetermined shape illustrated in FIG. 2 and/or the distal, stiffer portion 118 of the braid 110 illustrated in FIG. 1. The implant 100 can be selected for treatment such that the selected implant 100 has an outer segment 142 in the predetermined shape having a circumference greater than the circumference of the aneurysm sac 12, meaning the section 142' of the braid 110 contacting the aneurysm wall provides a force against the aneurysm wall 14 as it tends to expand to the predetermined shape. The implanted shape of the outer section 142' can thereby be smaller in circumference than the predetermined shape of the outer section 142.

Figure 3B:
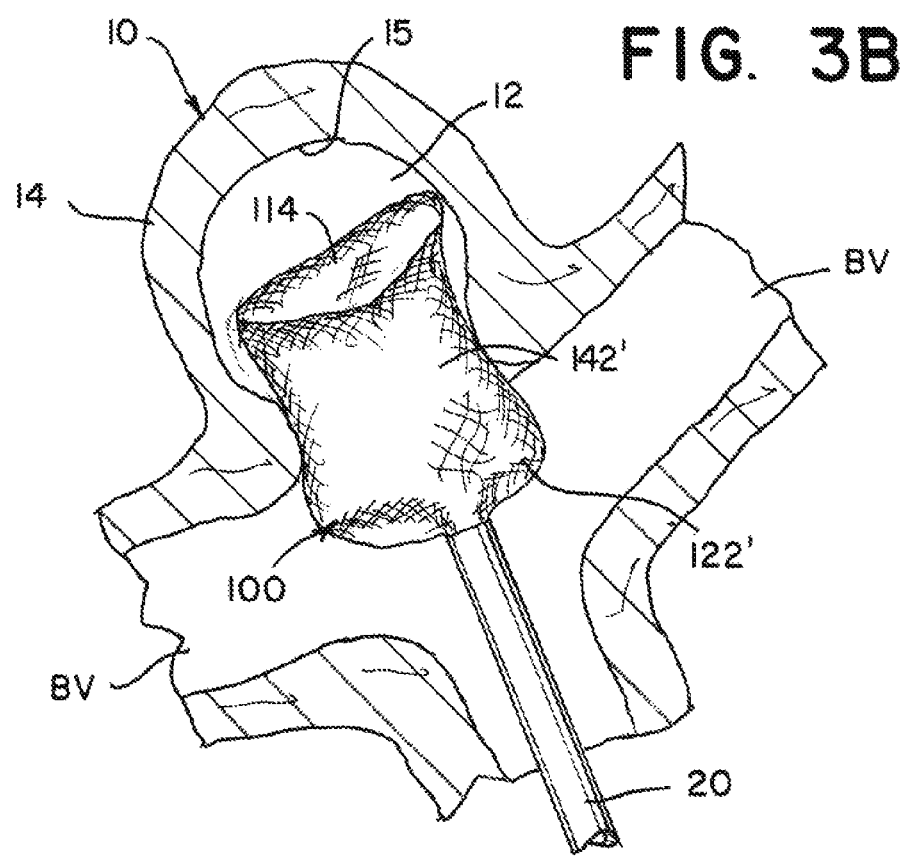

FIG. 3B illustrates the braid 110 inverting to form a proximal inversion 122' in the implanted shape. The proximal inversion 122' can correspond to the proximal inversion 122 in the predetermined shape.

Figure 3C:
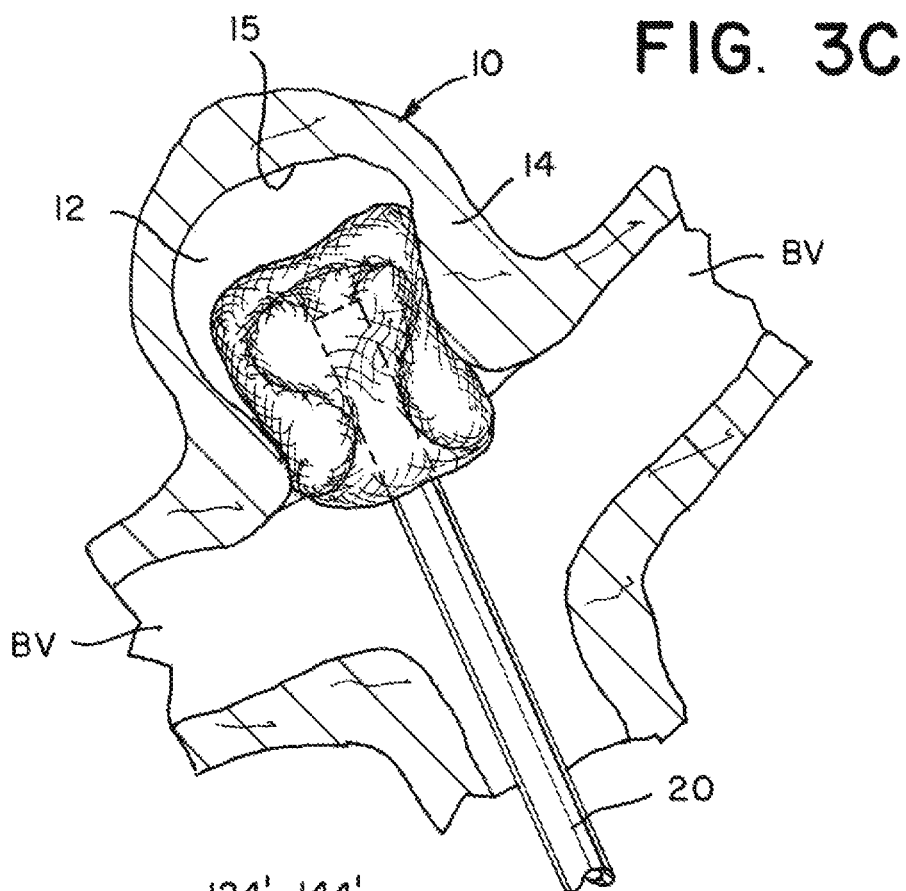

FIG. 3C illustrates the braid 110 expanding within the outer section 142'.

Figure 3D:
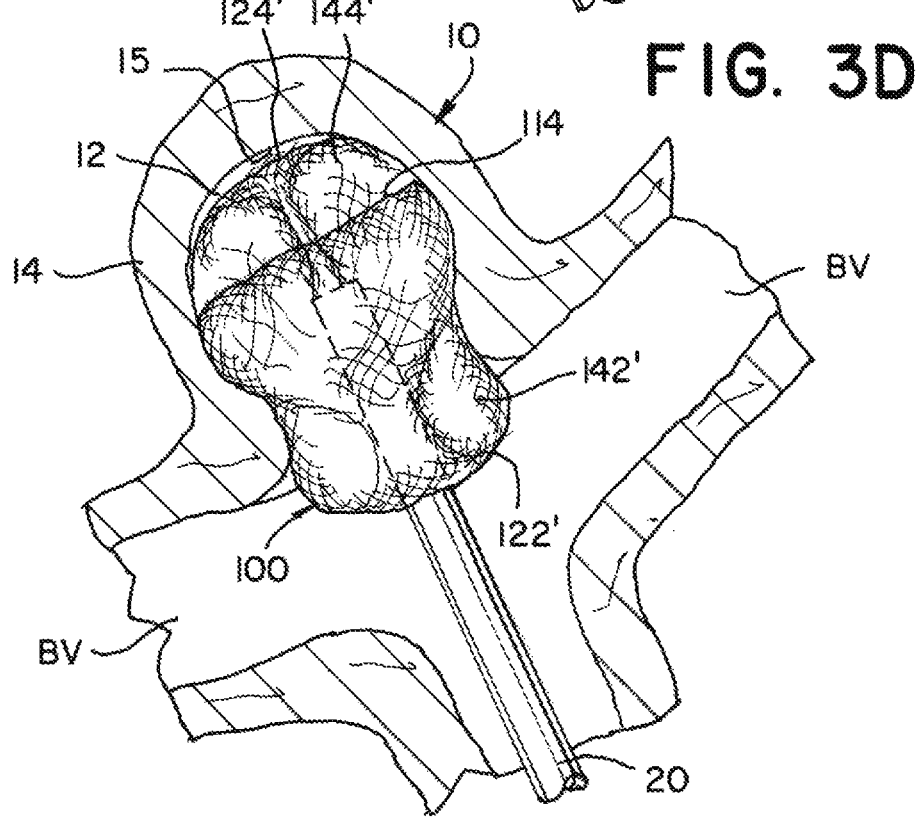

FIG. 3D illustrates the braid forming an inner sack 144' inside of the outer section 142'. A distal inversion 124' is illustrated positioned near a distal portion 15 of the aneurysm wall 14. The distal inversion 124' can correspond to a distal inversion 124 of the braid 110 in the predetermined shape. The inner sack 144' can correspond to the middle segment 144 in the predetermined shape illustrated in FIG. 2. The inner sack 144' can correspond to the stiff, distal portion 118 of the braid 110 illustrated in FIG. 1 and/or a portion of the braid 110 having less stiffness than the distal portion 118. The inner sack 144' can correspond to a portion of the braid 110 having greater stiffness than the flexible proximal portion 116 illustrated in FIG. 1.

Figure 3E:
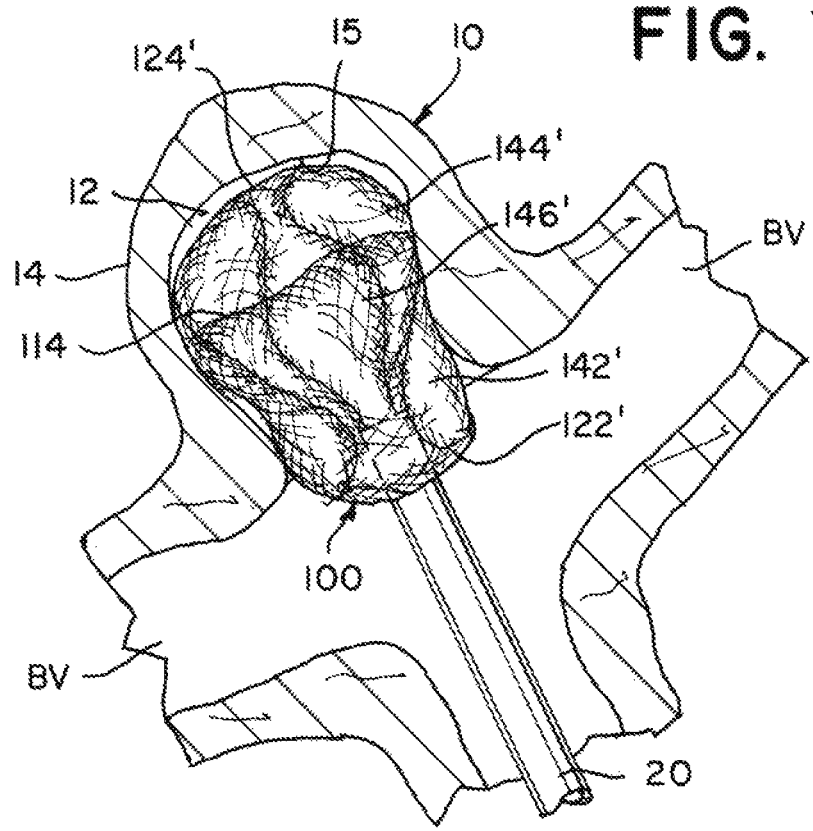

FIG. 3E illustrates a collapsible portion 146' of the braid 110 further exiting the catheter 20 and expanding within the inner sack 144'. The collapsible portion 146' can correspond to the inner segment 146 of the braid 110 in the predetermined shape. The collapsible portion 146' can correspond to the stiff, distal portion 118 of the braid 110 illustrated in FIG. 1 and/or a portion of the braid 110 having less stiffness than the distal portion. The collapsible portion 146' can correspond to a portion of the braid 110 having greater stiffness than the flexible proximal portion 116 illustrated in FIG. 1.

Figure 3F:
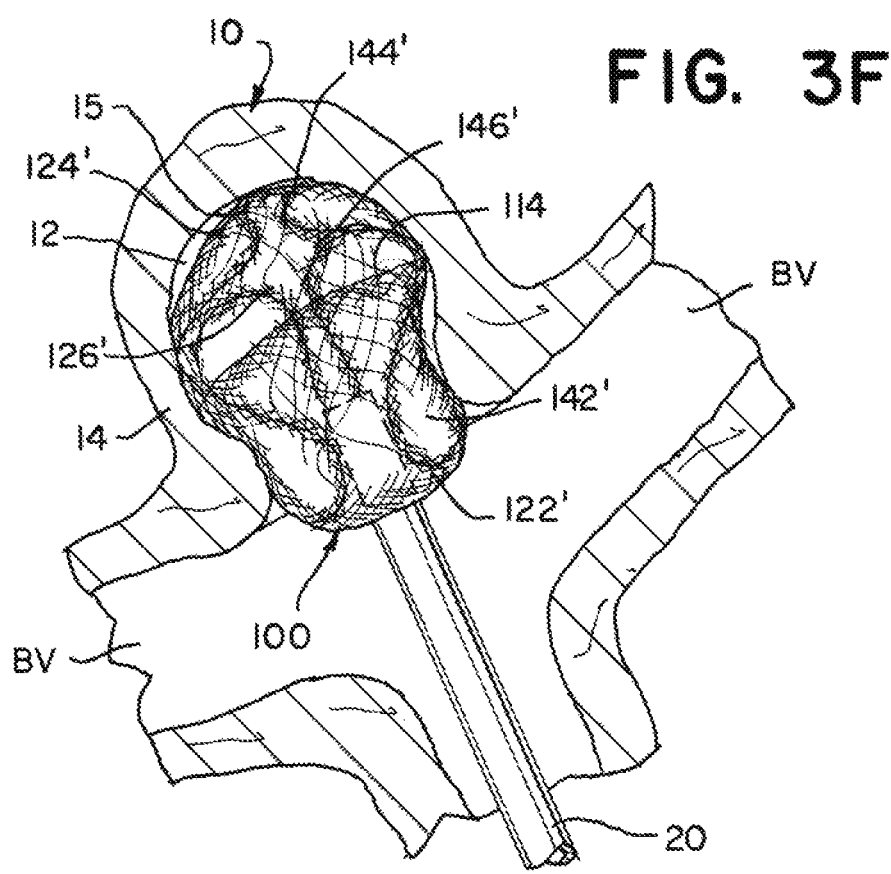

FIG. 3F illustrates the collapsible portion 146' forming a dome near the distal inversion 124'. A pinch point 126' is illustrated on the proximal side of the dome formed by the collapsible portion 146'. The pinch point 126' in the implanted shape can correspond to the pinch point 126 in the predetermined shape.

Figure 3G:
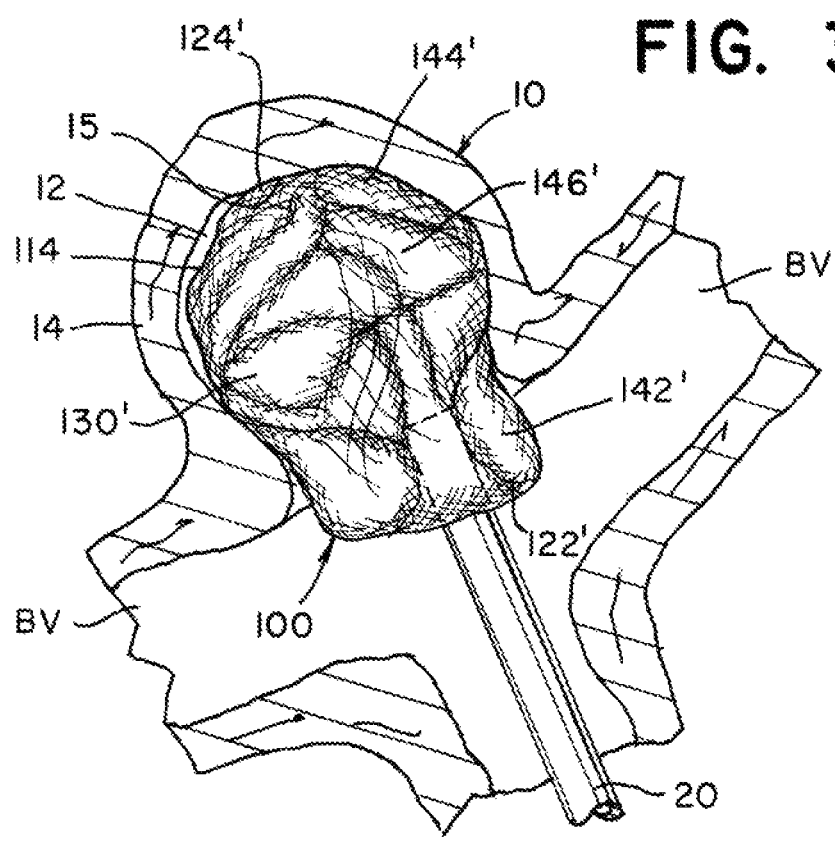

FIG. 3G illustrates a proximal tail 130' of the braid 110 flattening to a ribbon shape and folding within a space defined by the inner sack 144' and the dome of the collapsible portion 146'. The proximal tail 130' can correspond to the proximal tail 130 of the braid in the predetermined shape as illustrated in FIG. 2. The proximal tail 130' can correspond to the flexible, proximal portion 116 illustrated in FIG. 1.

Figure 3H:
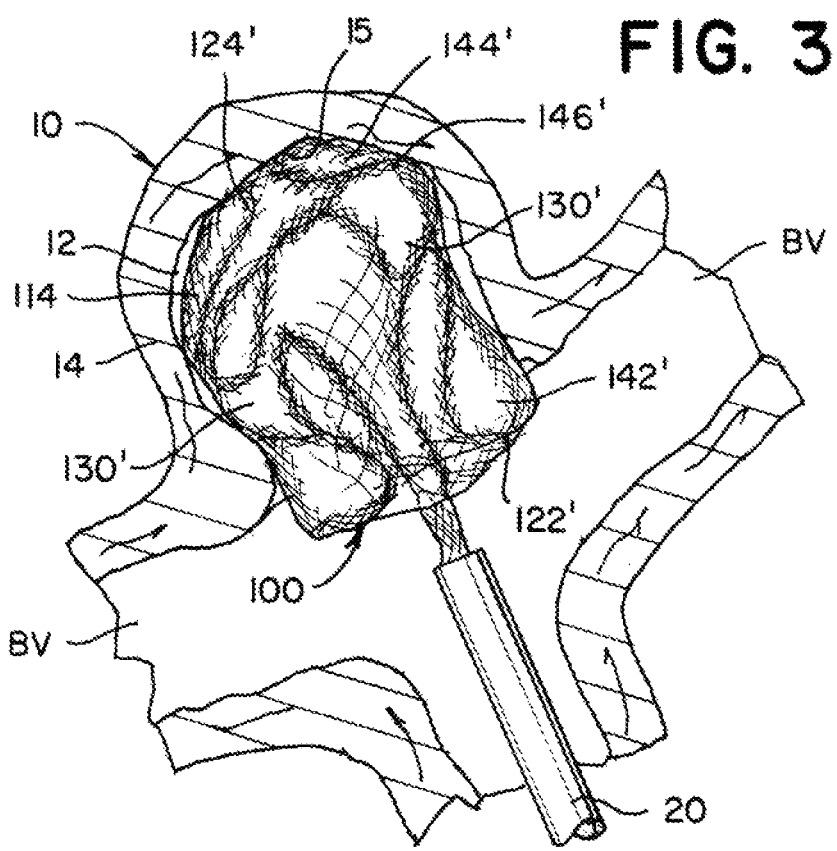

FIG. 3H illustrates additional length of the proximal tail 130' folding within the space defined by the inner sack 144' and the dome of the collapsible portion 146'.

Figure 3I:
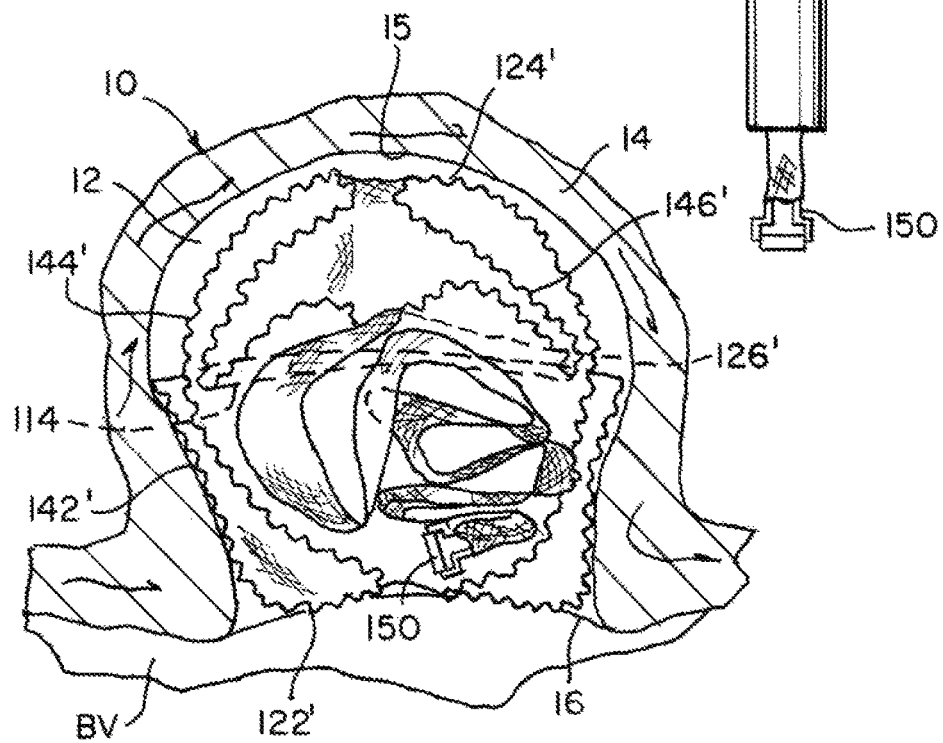

FIG. 3I illustrates the implant 100 in a final implanted shape. The outer section 142', inner sack 144', and collapsible portion 146' are illustrated in cross-section to better illustrate the folded ribbon shape of the proximal tail 130'.

Figure 4:
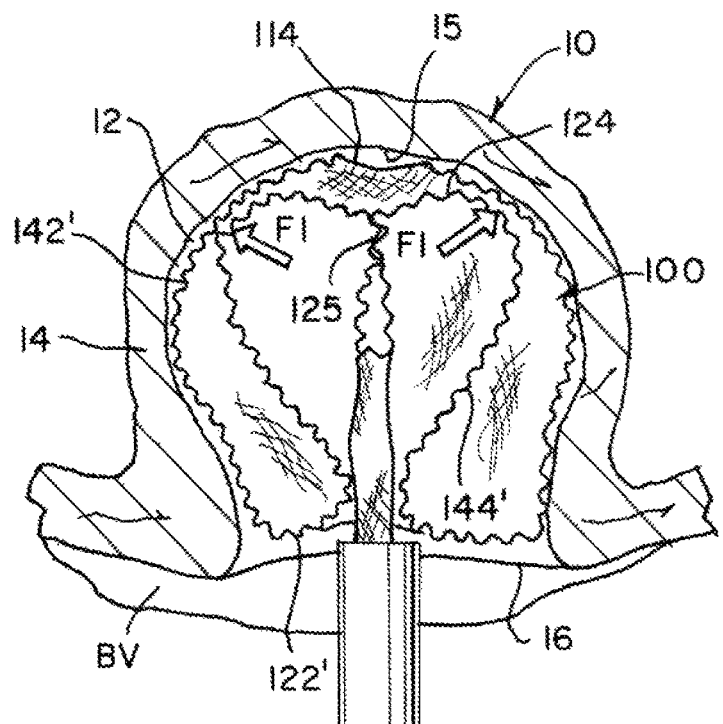
FIG. 4 is an illustration of an implant having a braid twisting near a distal inversion according to aspects of the present invention.

FIG. 4 illustrates an alternative implanted shape of a braid 110. As illustrated in FIG. 4, the braid 110 can include a twist 125 near the distal inversion 124'. Either with the twist 125 as illustrated in FIG. 4, or without the twist, as illustrated in FIG. 3I, the inner sack 144' can provide a force F1 pressing into the aneurysm wall 14 and/or the outer section 142', depending on the coverage of the outer section 142'. The outer section 142' is also illustrated in an alternative configuration such that the open end 114 is positioned approximate the distal portion 15 of the aneurysm wall 14.

Figure 5A:
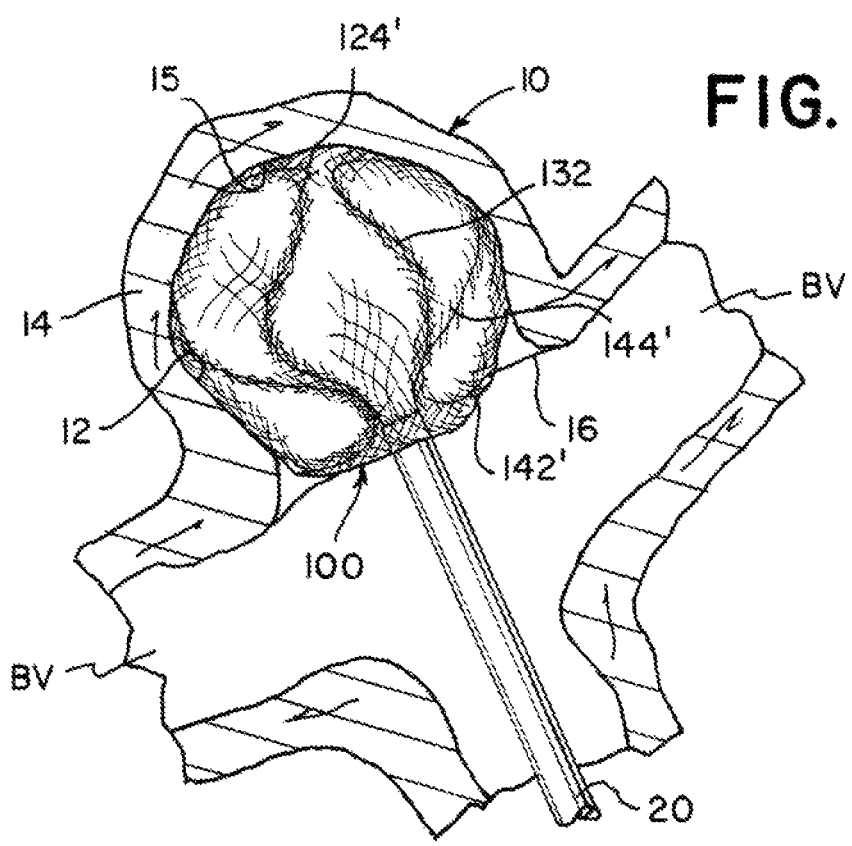
FIGS. 5A through 5B are illustrations of steps of an aneurysm treatment process according to aspects of the present invention.
Figure 5B:
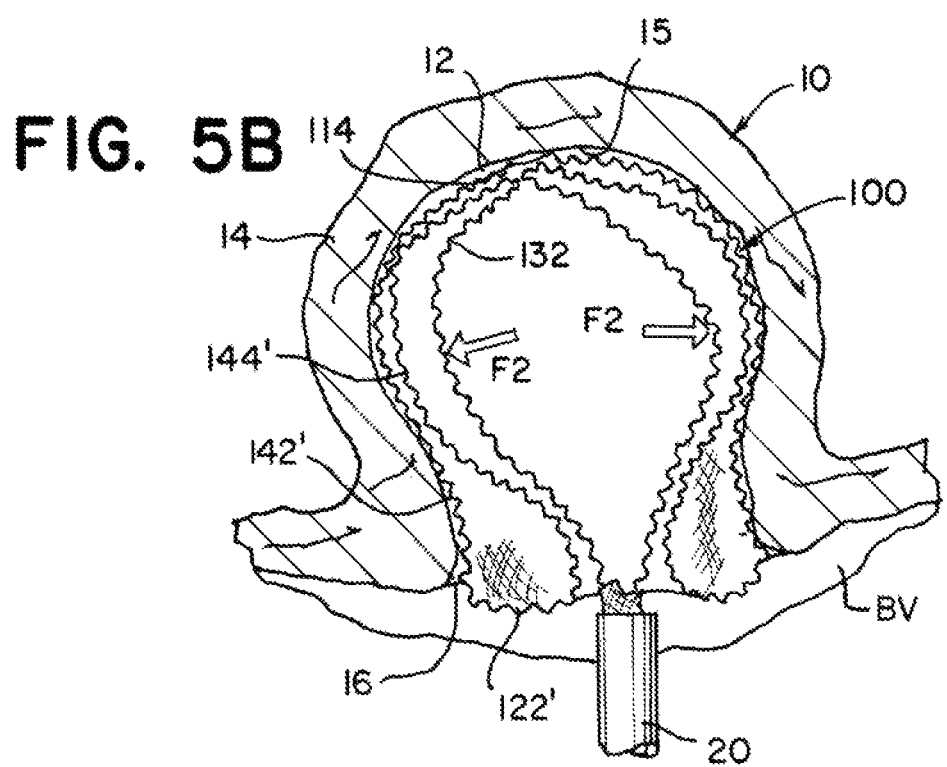

FIGS. 5A and 5B illustrate subsequent implantation steps of the implant 100 illustrated in FIG. 4. FIG. 5A illustrates a second inner sack 132 expanding within the aforementioned, first inner sack 144'. FIG. 5B illustrates the second inner sack 132 providing a second force F2 pressing into the first inner sack 144'. The braid 110 is illustrated in cross section in FIG. 5B. In subsequent implantation steps, the braid 110 can form additional nested sacks. Additionally, or alternatively, the braid can collapse to form a ribbon shape and fold into a space defined by one or more nested sacks similar to as illustrated in FIGS. 3G through 3I.

Figure 6:
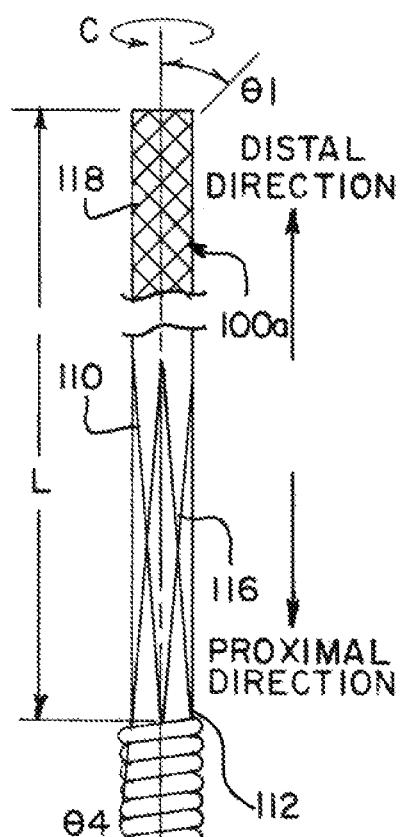
FIG. 6 is an illustration of an implant having a braid and an embolic coil each shaped for delivery through a catheter according to aspects of the present invention.

FIG. 6 illustrates an alternative implant 100a including a braid 110 having two sections 116, 118 of differing braid angle θ1, θ4, an embolic coil 160, and a detachment key 150. The embolic coil 160 can be attached to a proximal end 112 of the braid 110. A proximal portion 116 of the braid 110 near the proximal end 112 can have a small braid angle θ4. A distal portion 118 of the braid 110 near the distal end 114 of the braid can have a larger braid angle θ4. The braid 110 can be shaped into a single layer tubular shape as illustrated in FIG. 6. The braid can be shaped for delivery as described elsewhere herein.

Figure 7:
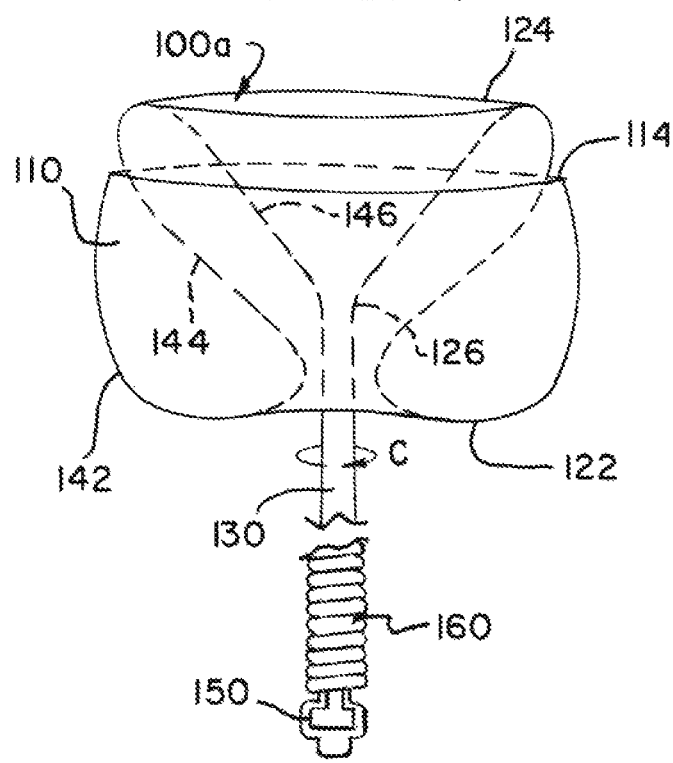
FIG. 7 is an illustration of an implant having a braid and an embolic coil with the braid in a predetermined shape according to aspects of the present invention.

FIG. 7 illustrates an alternative implant 100a such as the implant 100a illustrated in FIG. 6 having a braid 110 in a predetermined shape. The predetermined shape can have four sections 142, 144, 146, 130, two inversions 122, 124, and a pinch point 126 similar to as described in relation to FIG. 2. The embolic coil 160 can extend from the tail section 130 of the braid 110. When implanted, the embolic coil 160 can take the place of some or all of the tail portion 130' of the implant 100 illustrated in FIG. 3I.

Figure 8:
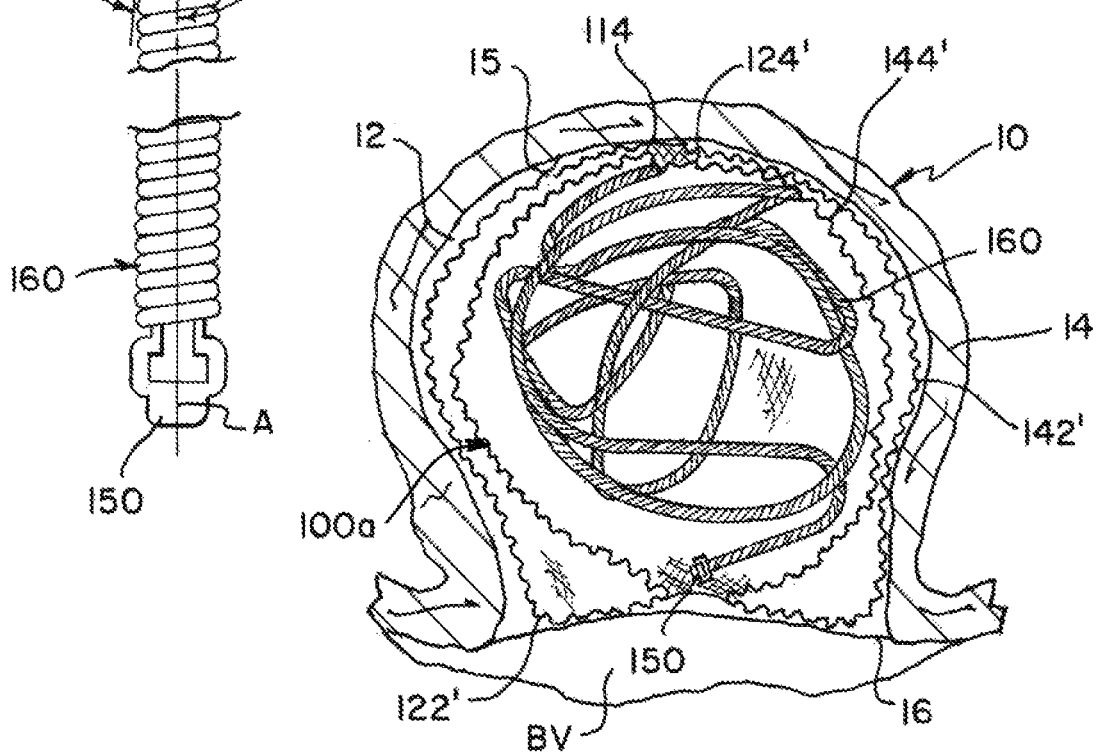
FIG. 8 is an illustration of an implant having a braid and an embolic coil implanted in an aneurysm according to aspects of the present invention.

FIG. 8 illustrates an implant 100a such as the implant 100a illustrated in FIG. 6 and/or FIG. 7 in an implanted shape. The braid 110 can have an outer section 142' and an inner sack 144' when implanted similar as disclosed in relation to FIG. 3I and/or FIG. 4. The embolic coil 160 can wind within the inner sack 144'.

Figure 9:
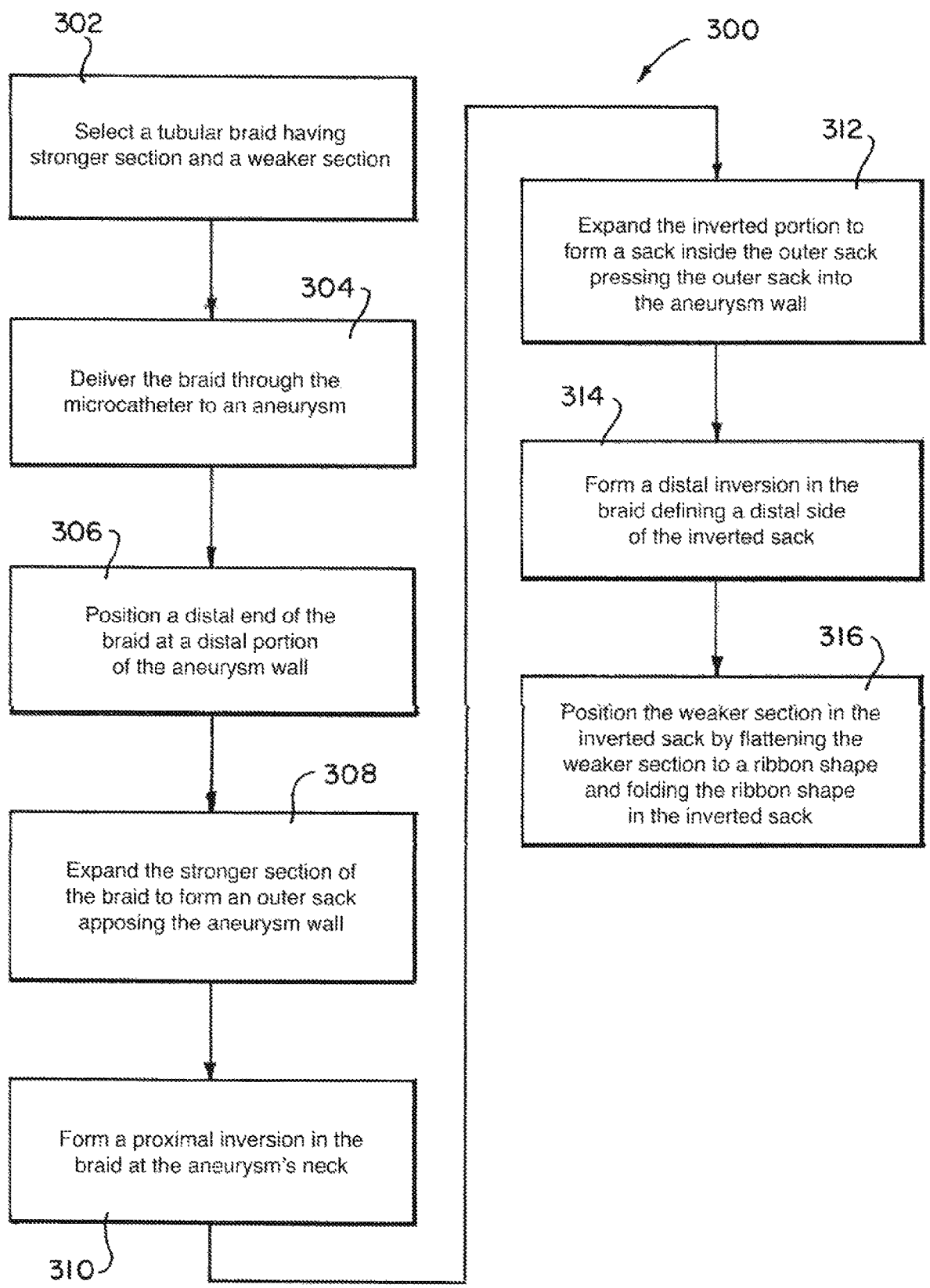
FIG. 9 is a flow diagram listing method steps that can be performed according to aspects of the present invention.

FIG. 9 is a flow diagram outlining example method steps for treating an aneurysm with an implant and/or system such as an example implant 100, 100a and/or system described herein, variations thereof, or alternative implant and/or system as would be appreciated and understood by a person ordinary skill in the art.

Referring to method 300 outlined in FIG. 9, in step 302 a tubular braid having a stronger section and a weaker section can be selected. The selected tubular braid can include an example tubular braid 110 as described herein, a variation thereof, or an alternative thereto as would be appreciated and understood by a person of ordinary skill in the art. The stronger section can have a larger braid angle relative to the weaker section such that the strength of the braid sections is respectively determined at least in part by the respective braid angles. Additionally, or alternatively, one or both of the stronger and weaker sections can be treated (e.g. heat treated) to modify material properties of one or both of the sections such that difference in strength between the two sections is determined at least in part by the treatment. Additionally, or alternatively, the stronger section can have a greater number of strands compared to the weaker section such that the strength of the braid sections is respectively determined at least in part by the number of strands. Additionally, or alternatively, the strands in the stronger section can have a larger diameter compared to the diameter of the strands in the weaker section such that the strength of the braid sections is respectively determined at least in part of the diameter of the strands. Additionally, or alternatively, the strands in the stronger section and the weaker section can include differing materials such that the strength of the sections is respectively determined at least in part by the material properties of the strands.

In step 304, the braid can be delivered through a microcatheter to an aneurysm. The braid can be detachably attached to an elongated delivery system. The implant (and thereby the braid) can be attached to the delivery system at a distal end of the delivery system. The delivery system and the implant can be positioned within the microcatheter such that the delivery system extends from a proximal end of the microcatheter. A user (e.g. physician) can deliver the implant through the microcatheter by manipulating the portion of the delivery system that extends out of the proximal end of the microcatheter. A user can place the implant similar to as illustrated in FIGS. 3A through 3I, FIG. 4, FIGS. 5A through 5B, and/or FIG. 8, otherwise described herein, or as otherwise understood by a person of ordinary skill in the art according to the teachings herein by manipulating the portion of the delivery system extending from the proximal end of the microcatheter.

In step 306, the distal end of the braid can be positioned at a distal portion 15 of the aneurysm wall 14. The distal end of the braid can be positioned as illustrated in FIG. 4, FIGS. 5A through 5B, and/or FIG. 8. Alternatively, the distal end of the braid can be positioned elsewhere, for instance within a middle third of the aneurysm wall 14, about half way between the distal portion 15 of the wall 14 and the aneurysm neck 16 as illustrated in FIGS. 3A through 3I.

In step 308, the stronger section of the braid can be expanded to form an outer sack apposing the aneurysm wall 14. The outer sack can be shaped similar to the outer sack 142' illustrated in FIG. 4, FIGS. 5A through 5B, and/or FIG. 8. Alternatively, the stronger section of the braid can be expanded to form a bowl shape similar to the outer section 142' shape illustrated in FIGS. 3A through 3I.

In step 310, a proximal inversion can be formed in the braid at the aneurysm's neck. The proximal inversion can be positioned similar to the proximal inversion 122' illustrated in FIGS. 3A through 3I, FIG. 4, FIGS. 5A through 5B, and/or FIG. 8. The proximal inversion can be shaped similar to the proximal inversion 122' illustrated in FIGS. 3A through 3I, FIG. 4, FIGS. 5A through 5B, and/or FIG. 8. The proximal inversion 122' can define a boundary between the outer sack or outer section expanded in step 308 and an inverted portion positioned within the outer sack or outer section.

In step 312, the inverted portion can be expanded to form a sack inside the outer sack or outer section. The inverted portion can press against the outer sack (or section), thereby pressing the outer sack (or section) into the aneurysm wall 14. The inverted portion can form an inner sack 144' such as illustrated in FIGS. 3A through 3I, FIG. 4, FIGS. 5A through 5B, and/or FIG. 8.

In step 314, a distal inversion can be formed in the braid. The distal inversion can define a distal side of the inverted, inner sack expanded in step 312. The distal inversion can define a boundary between the inner sack and an inner, non-inverted portion of the braid. The inner, non-inverted portion of the braid can include the weaker section of the braid.

In step 316, the weaker section of the braid can be positioned in the inverted sack. The weaker section can be flattened to a ribbon shape and folded into the inverted sack. The weaker section can be flattened and folded such as illustrated in FIGS. 3G through 3I, as otherwise described herein, and/or as understood by a person of ordinary skill in the art according to the teachings herein. The weaker section can correspond to the tail section 130, 130' of the braid 110.

The descriptions contained herein are examples of embodiments of the invention and are not intended in any way to limit the scope of the invention. The invention contemplates many variations and modifications of the implant, including: alternative delivery methods, alternative braid materials, alternative means for achieving a desired stiffness/flexibility of braid material, additional structures affixed to the implant (e.g. to aid in anchoring the implant, blood flow diversion, embolism formation, etc.), alternative predetermined braid shapes (e.g. one inversion, three inversions, four inversions, five or more inversions, non-radially symmetric shapes, alternative segment shapes, etc.), alternative implanted shapes, etc. Modifications apparent to one of ordinary skill in the art following the teachings of this disclosure are intended to be within the scope of the claims which follow.

What is claimed is:

1. A method comprising:
    selecting a substantially tubular braid comprising a first end, a second end, a length therebetween, a first portion extending from the first end, and a second portion extending from the second end such that the tubular braid is shapeable to a single layer cylindrical shape comprising a substantially uniform circumference along the length, a first braid angle in the first portion, and a second braid angle in the second portion, the second braid angle measuring less than the first braid angle;
    delivering the tubular braid through a microcatheter to an aneurysm;
    expanding the first portion of the braid to appose the aneurysm's wall;
    forming a proximal inversion of the braid approximate the aneurysm's neck;
    expanding an inverted portion of the braid to press the first portion to the aneurysm's wall;
    forming a distal inversion of the braid approximate the distal portion of the aneurysm's wall such that the inverted portion extends from the proximal inversion to the distal inversion;
    positioning the second portion of the braid within the inverted portion;
    twisting the braid approximate the distal inversion; and
    expanding the braid to form a sack within the inverted portion.

2. The method of claim 1, wherein selecting the substantially tubular braid further comprises selecting the tubular braid such that the single layer cylindrical shape further comprises a continuously decreasing braid angle extending from the first portion to the second portion.

3. The method of claim 1, wherein positioning the second portion of the braid further comprises flattening the second portion of the braid to a ribbon shape and looping the ribbon shape within the inverted portion.

4. The method of claim 1, further comprising:
shaping the braid to form a dome within the inverted portion, the dome positioned approximate the distal portion of the aneurysm wall.

5. The method of claim 1, wherein delivering the tubular braid further comprises delivering the tubular braid in the single layer cylindrical shape such that the first end is positioned in the distal direction in relation to the second end.

6. The method of claim 1, further comprising:
selecting an embolic coil;
positioning the embolic coil such that it is affixed to the tubular braid approximate the second end of the braid;
delivering the embolic coil through the microcatheter to the aneurysm; and
positioning the embolic coil within the inverted portion.

7. An implant comprising:
a substantially tubular braid shapeable to a single layer cylindrical shape and movable to an implanted shape, the braid comprising:
a first end;
a second end;
a length measurable from the first end to the second end;
a first portion extending from the first end;
a second portion extending from the second end;
the single layer cylindrical shape comprises a substantially uniform circumference along the length, a first braid angle in the first portion, and a second braid angle in the second portion, the second braid angle measuring less than the first braid angle; and
wherein, in the implanted shape, the first portion is configured to be positioned to appose an aneurysm wall, an inverted sack is formed by a proximal inversion of the braid approximate an aneurysm neck, the inverted sack being expandable and positioned to press the first portion to the aneurysm wall, and the second portion is positioned within the inverted sack,
wherein, in the implanted shape, the second portion is configured to be expanded to form an inner sack, the inner sack is positioned to press the inverted sack to the first portion, the braid comprises a distal inversion configured to be approximate the distal portion of the aneurysm wall such that the inverted sack extends from the proximal inversion to the distal inversion and separates the inner sack and the inverted sack, wherein the first end terminates proximal of the distal inversion, and the braid is twisted approximate the distal inversion.

8. The implant of claim 7,
wherein, in the single layer cylindrical shape, the braid comprises a continuously decreasing braid angle extending from the first portion to the second portion.

9. The implant of claim 7, wherein, in the implanted shape, at least a portion of the second portion of the braid is looped within the distal inversion.

10. The implant of claim 7,
wherein, when the braid is in the single layer cylindrical shape, the braid is sized to be delivered through a microcatheter to an aneurysm, and
wherein the braid is movable from the single layer cylindrical shape to the implanted shape.

11. The implant of claim 7, further comprising:
an embolic coil affixed to the tubular braid approximate the second end of the braid,
wherein, in the implanted shape, the braid is shaped to allow the embolic coil to be positioned within the inverted sack.

* * * * *